US008227228B2

(12) United States Patent
Kanamaru et al.

(10) Patent No.: US 8,227,228 B2
(45) Date of Patent: Jul. 24, 2012

(54) D-AMINO ACID OXIDASE, AND METHOD FOR PRODUCTION OF L-AMINO ACID, 2-OXO ACID, OR CYCLIC IMINE

(75) Inventors: Hiroyuki Kanamaru, Takasago (JP); Makoto Ueda, Takasago (JP); Ryuuji Miki, Takasago (JP); Hirokazu Nanba, Takasago (JP)

(73) Assignee: Kaneka Corporation, Osaka (JP)

( * ) Notice: Subject to any disclaimer, the term of this patent is extended or adjusted under 35 U.S.C. 154(b) by 1030 days.

(21) Appl. No.: 11/997,861

(22) PCT Filed: Aug. 2, 2006

(86) PCT No.: PCT/JP2006/315285
§ 371 (c)(1),
(2), (4) Date: Feb. 4, 2008

(87) PCT Pub. No.: WO2007/015511
PCT Pub. Date: Feb. 8, 2007

(65) Prior Publication Data
US 2011/0086396 A1    Apr. 14, 2011

(30) Foreign Application Priority Data

Aug. 2, 2005  (JP) ................................. 2005-224505
Apr. 24, 2006  (JP) ................................. 2006-119408

(51) Int. Cl.
| | |
|---|---|
| *C12N 9/02* | (2006.01) |
| *C12N 15/00* | (2006.01) |
| *C12N 1/20* | (2006.01) |
| *C12P 21/06* | (2006.01) |
| *C12P 19/34* | (2006.01) |
| *C12P 13/04* | (2006.01) |
| *C07H 21/04* | (2006.01) |
| *C07K 1/00* | (2006.01) |

(52) U.S. Cl. ... 435/189; 435/69.1; 435/91.1; 435/320.1; 435/252.3; 435/106; 536/23.1; 536/23.2; 530/350

(58) Field of Classification Search .................. 435/189, 435/69.1, 91.1, 320.1, 252.3, 106; 536/23.1, 536/23.2; 530/350
See application file for complete search history.

(56) References Cited

U.S. PATENT DOCUMENTS

| | | | |
|---|---|---|---|
| 4,849,345 A | 7/1989 | Asano et al. | |
| 4,970,157 A | 11/1990 | Hibino et al. | |
| 5,208,155 A | 5/1993 | Mosbach et al. | |
| 6,187,574 B1 | 2/2001 | Garcia Lopez et al. | |
| 7,217,544 B2 | 5/2007 | Hummel et al. | |
| 2006/0063238 A1 | 3/2006 | Hummel et al. | |
| 2008/0050819 A1 | 2/2008 | Hillebrand et al. | |

FOREIGN PATENT DOCUMENTS

| | | |
|---|---|---|
| DE | 10 2004 008 445 A1 | 2/2004 |
| EP | 0 364 275 B1 | 4/1990 |
| JP | 62-501677 | 7/1987 |
| JP | 62-244386 A | 10/1987 |
| JP | 63-071180 A | 3/1988 |
| JP | 63-157986 A | 6/1988 |
| JP | 11-318439 A | 11/1999 |
| WO | 97/40171 A1 | 10/1997 |
| WO | 2005/090581 A1 | 9/2005 |
| WO | 2005/090590 A1 | 9/2005 |
| WO | 2005/093081 A1 | 10/2005 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol.,2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Kimchi-Sarfaty et al., A "Silent" polymorphism in the MDR1 gene changes substrate specificty. Science, 2007, vol. 315: 525-528.*

(Continued)

*Primary Examiner* — Ganapathirama Raghu
(74) *Attorney, Agent, or Firm* — Sughrue Mion, PLLC

(57) ABSTRACT

The present invention relates to novel D-amino acid oxidase isolated and purified from *Candida intermedia*, a gene encoding the D-amino acid oxidase, a recombinant plasmid containing the gene, and a transformant into which the D-amino acid oxidase gene has been introduced, as well as a production method of D-amino acid oxidase including culturing the transformant. Moreover, the present invention relates to a production method of L-amino acids, 2-oxo acids or cyclic imines, which include reacting racemic amino acids with the D-amino acid oxidase, more preferably, a production method of L-amino acids, which includes reacting racemic amino acid with the D-amino acid oxidase, amino acid dehydrogenase and an enzyme having a coenzyme-regenerating activity. According to the present invention, L-amino acids, 2-oxo acids or cyclic imines can be produced with good efficiency in an industrial scale.

8 Claims, 6 Drawing Sheets

OTHER PUBLICATIONS

Nackley et al., Human Caechol-O-Methytransferase haplotypes modulate protein expression by altering mRNA secondary structure. Science, 2006, vol. 314: 1930-1933.*

Sauna et al., Silent polymorhisms speak: How they affect pharmacogenomics and the treatment of cancer. Cancer Res., 2007, vol. 67(20): 9609-9612.*

H. Yurimoto, et al, "Physiological Role of the D-amino Acid Oxidase Gene, DAO1, in Carbon and Nitrogen Metabolism in the Methylotrophic Yeast *Candida boidinii*", Yeast, 2000, p. 1217-1227, vol. 16, No. 13.

M. Yoshizawa, et al, "Some Properties of Peroxisome-Associated D Amino Acid Oxidase From *Candida-tropicalis*", Agric Biol Chem, 1986, p. 2637-2638; p. 2637, vol. 50, No. 10.

M. Gabler, et al, "Detection and Substrate Selectivity of New Microbial D-amino Acid Oxidases", Enzyme and Microbial Technology, 2000, p. 605-611, vol. 27, No. 8.

B. Nidetzky, et al, "Binding Energy and Specificity in the Catalytic Mechanism of Yeast Aldose Reductases", Biochem J, 1999, p. 101-107, vol. 344.

N. Nakajima, et al, "Enzymatic Conversion of Racemic Methionine to the L-Enantiomer", J Chem Soc Chem Commun, 1990, p. 947-948, No. 13.

H. Yurimoto, et al, "Characterization and High-Level Production of D-Amino Acid Oxidase in *Candida boidinii*", Biosci Biotechnol Biochem, 2001, p. 627-633, vol. 65, No. 3.

R. Bode, et al, "D Amino Acid Oxidase Aromatic L Amino Animotransferase and Aromatic Lactate Dehydrogenase From Several Yeast Species Comparison of Enzyme Activities and Enzyme Specificities", Acta BioTechnologica, 1987, p. 221-225, vol. 7, No. 3.

Kawamoto et al, "Production of D-amino Acid Oxidase by *Candida tropicalis*," J. Ferment. Technol., 55:13-18 (1977).

Patel, "Enzymatic synthesis of chiral intermediates for omapatrilat, and antihypertensive drug," *Biomolecular Engineering* 17:167-182 (2001).

Database UniProt [Online] Aug. 16, 2004, "SubName: Full=DEHA2E12760p;" XP002510645 retrieved from EBI accession No. UNIPROT:Q6BPK9 Database accession No. Q6BPK9 see sequence.

Database UniProt [Online] Mar. 1, 2001, "SubName: Full=D-amino acid oxidase; EC=<AHREF="http://srs.ebi.ac.uk/srsbin/cgi-bin/wgetz?[enzyme-ECNumber:1.4.3.3]+-e">1.4.3. 3</A>;" XP002510647 retrieved from EBI accession No. UNIPROT:Q9HGY3 Database accession No. Q9HGY3 see sequence.

Tishkov, et al., "D-Amino Acid Oxidase: Structure, Catalytic Mechanism, and Practical Application," *Biochemistry* (Moscow) 70:40-54 (2005).

Nakajima, et al., "Enzymatic Conversion of Racemic Methionine to the $_L$-Enantiomer," *J. Chem. Soc. Commun.* 13:947-948 (1990).

Pollegioni, et al., "Properties and applications of microbial-D-amino acid oxidases: current state and perspectives," *Appl. Micribiol. Biotechnol.* 78:1-16 (2008).

Yurimoto, et al., "Physiological role of the D-amino acid oxidase gene, *DAOI*, in carbon and nitrogen metabolism in the methylotrophic yeast *Candida boidinii*," *Yeast* 16:1217-1227 (2000).

Yoshizawa, et al., "Some Properties of Peroxisome-associated D-Amino Acid Oxidase from *Candida tropicalis*," *Agric. Biol. Chem.* 50:2637-2638 (1986).

Gabler, et al., "Detection and substrate selectivity of new microbial D-amino acid oxidases," *Enzyme and Microbial Technology* 27:605-611 (2000).

Nidetzky, et al., "Binding energy and specificity in the catalytic mechanism of yeast aldose reductases," *Biochem. J.* 344:101-107 (1999).

Yurimoto, et al., "Characterization and High-level Production of D-Amino Acid Oxidase in *Candida boidinii*," *Biosci. Biotechnol. Biochem.* 65(3):627-633 (2001).

Bode et al., "D-Amino Acid Oxidase, Aromatic L-Amino Aminotransferase, and Aromatic Lactate Dehydrogenase from Several Yeast Species: Comparison of Enzyme Activities and Enzyme Specificities," *Acta Biotechnol.* 7(3):221-225 (1987).

* cited by examiner

SEQUENCE LISTING

```
<160> NUMBER OF SEQ ID NOS: 23

<210> SEQ ID NO 1
<211> LENGTH: 344
<212> TYPE: PRT
<213> ORGANISM: Candida intermedia

<400> SEQUENCE: 1

Met Ser Glu Tyr Val Ile Val Gly Ser Gly Ile Ile Gly Leu Tyr Thr
1               5                  10                  15

Gly Tyr Lys Leu Leu Glu Ser Gly Val Pro Gly Glu Ser Ile Thr Val
            20                  25                  30

Glu Ala Glu Phe Leu Pro Gly Asp Glu Ser Ile Lys Tyr Thr Ser Pro
        35                  40                  45

Tyr Ala Gly Gly Asn Phe Ser Gly Ile Thr Gly Asp Asp Pro Asp Ser
    50                  55                  60

Leu Lys Phe Asp Lys His Thr Tyr Glu Asn Leu Pro Lys Leu Gln Lys
65                  70                  75                  80

Leu Leu Gly Gly Pro Leu Cys Gly Leu Asp Met Leu Pro Ala Thr Glu
                85                  90                  95

Ile Trp Asp Asn Val Lys Ser Lys Lys Ile Asp Ser Leu Lys Gln Tyr
            100                 105                 110
```

```
Leu Lys Asp Tyr Gln Glu Ile Glu Gln Glu Glu Leu Pro Glu Gly Ala
        115                 120                 125

Lys Phe Gly Val Lys Phe Thr Thr Trp Asn Phe Asn Cys Pro Lys Phe
    130                 135                 140

Leu Ser Asn Val Gln Lys Tyr Leu Leu Ser Lys Asn Val Thr Phe Ile
145                 150                 155                 160

Arg Lys Asn Leu Thr His Ile Thr Gln Ala Phe Gly Pro Ala Thr Lys
                165                 170                 175

Cys Val Phe Asn Cys Thr Gly Asn Gly Ala Arg Phe Leu Gly Gly Val
            180                 185                 190

Gln Asp Ala Lys Val Tyr Pro Thr Arg Gly Gln Val Val Val Ile Lys
        195                 200                 205

Ala Pro His Ile Asn Glu Asn Met Ile Arg Trp Gly Asp Asn Tyr Ala
    210                 215                 220

Thr Tyr Ile Ile Lys Arg Pro Tyr Ser His Asp Gln Leu Ile Leu Gly
225                 230                 235                 240

Gly Phe Leu Gln Lys Asp Trp Thr Pro Asp Thr Leu Ser Glu Gln
                245                 250                 255

Thr Glu Asp Ile Leu Phe Arg Thr Thr Asn Leu Leu Pro Lys Ile Leu
            260                 265                 270

Asn Gln Asn Pro His Gly Pro Asn Ile Glu Asp Leu Glu Ile Val Arg
        275                 280                 285

Val Val Ala Gly Leu Arg Pro Ser Arg His Gly Val Arg Ile Glu
    290                 295                 300

Lys Glu Val Leu Asp Gly Lys Leu Leu Ile His Asn Tyr Gly Ala Gly
305                 310                 315                 320

Gly Tyr Gly Tyr Gln Ser Gly Leu Gly Met Ala Asp Lys Ala Val Lys
                325                 330                 335

Leu Ala Leu Gly Gln Ser Lys Leu
                340
```

<210> SEQ ID NO 2
<211> LENGTH: 1035
<212> TYPE: DNA
<213> ORGANISM: Candida intermedia

<400> SEQUENCE: 2

```
atgtctgaat acgtaattgt tggttctggt atcataggct gtacactgg  atacaaactt        60 ctagagtctg gagtgcccgg tgaatccatc actgttgagg cagaattctt acctggggac       120
gagtctatca aatacacttc tccttatgcg ggaggaaatt tctccggaat cactggtgat       180
gatcctgact cgttgaagtt cgataagcac acctacgaaa acttgcccaa gttgcaaaag       240
cttttgggtg ggccactgtg tggcttagat atgctccctg ctaccgaaat ctgggataat       300
gtcaagtcga agaaaattga ctcttttgaag cagtatctta aggactacca ggaaattgag       360
caagaagaat gcctgagggg tgccaagttt ggagtgaaat tcaccacctg aacttcaat       420 tgtcccaagt ttttgagtaa tgtccagaaa taccttcttt ccaagaatgt cacttttcatc      480 cgtaaaaact tgacccatat aactcaagca tttggtcctg caaccaaatg tgtgttcaat       540
tgcactggaa atggtgcccg attccttggt ggagttcagg acgccaaagt gtatcctaca       600
agaggacagg tggttgtcat taaggctccc cacatcaatg aaacatgat  agatggggc        660 gataactatg ccacttacat aatcaaaaga ccatactcac atgatcagtt gattcttgga       720
ggttttctcc agaagacga  ctggactcca gatactcttt ctgagcaaac agaagatata       780
cttttcagaa caactaatct attgccaaag atcttaaacc agaatccaca tgggccaaac       840
```

-continued

```
attgaagatt tggaaattgt gagagtggtg gctggattgc gtcccagcag acatggaggt    900
gtcagaattg aaaaagaggt gctagatgga aagttgttga ttcacaatta cggtgctgga    960
gggtatggat atcaatcggg tttgggaatg gcagataaag ctgtgaagtt agcattgggc   1020
cagagtaaac tttag                                                    1035

<210> SEQ ID NO 3
<211> LENGTH: 17
<212> TYPE: DNA
<213> ORGANISM: Artificial
<220> FEATURE:
<223> OTHER INFORMATION: Primer-1
<220> FEATURE:
<221> NAME/KEY: misc_feature
<222> LOCATION: (15)..(15)
<223> OTHER INFORMATION: n represents a, t, g or c

<400> SEQUENCE: 3
rcwwswccwt gggcngg                                                    17

<210> SEQ ID NO 4
<211> LENGTH: 17
<212> TYPE: DNA
<213> ORGANISM: Artificial
<220> FEATURE:
<223> OTHER INFORMATION: Primer-2

<400> SEQUENCE: 4
gcrkswccrt arttrtg                                                    17

<210> SEQ ID NO 5
<211> LENGTH: 20
<212> TYPE: DNA
<213> ORGANISM: Artificial
<220> FEATURE:
<223> OTHER INFORMATION: Primer-3

<400> SEQUENCE: 5
tctttctgag caaacagaag                                                 20

<210> SEQ ID NO 6
<211> LENGTH: 20
<212> TYPE: DNA
<213> ORGANISM: Artificial
<220> FEATURE:
<223> OTHER INFORMATION: Primer-4

<400> SEQUENCE: 6
gacattatcc cagatttcgg                                                 20

<210> SEQ ID NO 7
<211> LENGTH: 1084
<212> TYPE: DNA
<213> ORGANISM: Candida intermedia

<400> SEQUENCE: 7
atgtctgaat acgtaattgt tgggtatgtc caatgggttt gttctgcttt aaacatctgt     60
ttctaacctc agttctggta tcataggctt gtacactgga tacaaacttc tagagtctgg   120
agtgcccggt gaatccatca ctgttgaggc agaattctta cctggggacg agtctatcaa   180
atacacttct ccttatgcgg gaggaaattt ctccggaatc actggtgatg atcctgactc   240
gttgaagttc gataagcaca cctacgaaaa cttgcccaag ttgcaaaagc ttttgggtgg   300
gccactgtgt ggcttagata tgctccctgc taccgaaatc tgggataatg tcaagtcgaa   360
```

```
gaaaattgac tctttgaagc agtatcttaa ggactaccag gaaattgagc aagaagaatt    420
gcctgagggt gccaagtttg gagtgaaatt caccacctgg aacttcaatt gtcccaagtt    480
tttgagtaat gtccagaaat accttctttc caagaatgtc actttcatcc gtaaaaactt    540
gacccatata actcaagcat ttggtcctgc aaccaaatgt gtgttcaatt gcactggaaa    600
tggtgcccga ttccttggtg gagttcagga cgccaaagtg tatcctacaa gaggacaggt    660
ggttgtcatt aaggctcccc acatcaatga gaacatgatt agatggggcg ataactatgc    720
cacttacata atcaaaagac atactcaca tgatcagttg attcttggag gttttctcca    780
gaaagacgac tggactccag atactctttc tgagcaaaca gaagatatac ttttcagaac    840
aactaatcta ttgccaaaga tcttaaacca gaatccacat gggccaaaca ttgaagattt    900
ggaaattgtg agagtggtgg ctggattgcg tcccagcaga catggaggtg tcagaattga    960
aaaagaggtg ctagatggaa agttgttgat tcacaattac ggtgctggag ggtatggata   1020
tcaatcgggt ttgggaatgg cagataaagc tgtgaagtta gcattgggcc agagtaaact   1080
ttag                                                                1084
```

```
<210> SEQ ID NO 8
<211> LENGTH: 30
<212> TYPE: DNA
<213> ORGANISM: Artificial
<220> FEATURE:
<223> OTHER INFORMATION: Primer-5

<400> SEQUENCE: 8
cgcactccat atgtctgaat acgtaattgt                                      30

<210> SEQ ID NO 9
<211> LENGTH: 32
<212> TYPE: DNA
<213> ORGANISM: Artificial
<220> FEATURE:
<223> OTHER INFORMATION: Primer-6

<400> SEQUENCE: 9
gacacggagc tcttaaagtt tactctggcc ca                                   32

<210> SEQ ID NO 10
<211> LENGTH: 31
<212> TYPE: DNA
<213> ORGANISM: Artificial
<220> FEATURE:
<223> OTHER INFORMATION: Primer-7

<400> SEQUENCE: 10
atcgttacat atgagcttag tagaaaaaac a                                    31

<210> SEQ ID NO 11
<211> LENGTH: 30
<212> TYPE: DNA
<213> ORGANISM: Artificial
<220> FEATURE:
<223> OTHER INFORMATION: Primer-8

<400> SEQUENCE: 11
taactgcagt tattagttgc gaatatccca                                      30

<210> SEQ ID NO 12
<211> LENGTH: 43
<212> TYPE: DNA
<213> ORGANISM: Artificial
```

```
<220> FEATURE:
<223> OTHER INFORMATION: Primer-9

<400> SEQUENCE: 12
actgaattct aaggaggtta acaatggaac tttttaaata tat          43

<210> SEQ ID NO 13
<211> LENGTH: 32
<212> TYPE: DNA
<213> ORGANISM: Artificial
<220> FEATURE:
<223> OTHER INFORMATION: Primer-10

<400> SEQUENCE: 13
gatgagctct tattaacgtc tgcttaatac ac                      32

<210> SEQ ID NO 14
<211> LENGTH: 43
<212> TYPE: DNA
<213> ORGANISM: Artificial
<220> FEATURE:
<223> OTHER INFORMATION: Primer-11

<400> SEQUENCE: 14
cggggtacct aaggaggtta acaatgtctg aatacgtaat tgt          43

<210> SEQ ID NO 15
<211> LENGTH: 29
<212> TYPE: DNA
<213> ORGANISM: Artificial
<220> FEATURE:
<223> OTHER INFORMATION: Primer-12

<400> SEQUENCE: 15
gcgggatcct taaagtttac tctggccca                          29

<210> SEQ ID NO 16
<211> LENGTH: 43
<212> TYPE: DNA
<213> ORGANISM: Artificial
<220> FEATURE:
<223> OTHER INFORMATION: Primer-13

<400> SEQUENCE: 16
aaactgcagt aaggaggtta acaatgtctg aatacgtaat tgt          43

<210> SEQ ID NO 17
<211> LENGTH: 29
<212> TYPE: DNA
<213> ORGANISM: Artificial
<220> FEATURE:
<223> OTHER INFORMATION: Primer-14

<400> SEQUENCE: 17
aaactgcagt taaagtttac tctggccca                          29

<210> SEQ ID NO 18
<211> LENGTH: 27
<212> TYPE: DNA
<213> ORGANISM: Artificial
<220> FEATURE:
<223> OTHER INFORMATION: Primer-15

<400> SEQUENCE: 18
atcacgcata tggcgaaaat actttgc                            27
```

```
<210> SEQ ID NO 19
<211> LENGTH: 30
<212> TYPE: DNA
<213> ORGANISM: Artificial
<220> FEATURE:
<223> OTHER INFORMATION: Primer-16

<400> SEQUENCE: 19
atagaattct tatcagccgg ccttcttgaa                              30

<210> SEQ ID NO 20
<211> LENGTH: 44
<212> TYPE: DNA
<213> ORGANISM: Artificial
<220> FEATURE:
<223> OTHER INFORMATION: Primer-17

<400> SEQUENCE: 20
tacgaattct aaggaggtta acaatgagct tagtagaaaa aaca              44

<210> SEQ ID NO 21
<211> LENGTH: 30
<212> TYPE: DNA
<213> ORGANISM: Artificial
<220> FEATURE:
<223> OTHER INFORMATION: Primer-18

<400> SEQUENCE: 21
taactgcagt tattagttgc gaatatccca                              30

<210> SEQ ID NO 22
<211> LENGTH: 31
<212> TYPE: DNA
<213> ORGANISM: Artificial
<220> FEATURE:
<223> OTHER INFORMATION: Primer-19

<400> SEQUENCE: 22
ttcatcgcat atggaattcg agctcggtac c                            31

<210> SEQ ID NO 23
<211> LENGTH: 26
<212> TYPE: DNA
<213> ORGANISM: Artificial
<220> FEATURE:
<223> OTHER INFORMATION: Primer-20

<400> SEQUENCE: 23
ttcatcgcat atgtgtttcc tgtgtg                                  26
```

D-AMINO ACID OXIDASE, AND METHOD FOR PRODUCTION OF L-AMINO ACID, 2-OXO ACID, OR CYCLIC IMINE

TECHNICAL FIELD

The present invention relates to novel D-amino acid oxidase produced by a microorganism, DNA encoding same and method for production of D-amino acid oxidase using a microorganism or transformant having an ability to produce D-amino acid oxidase, as well as an efficient production method of L-amino acid, 2-oxo acid or cyclic imine, which uses D-amino acid oxidase.

CROSS-REFERENCE TO THE RELATED APPLICATION

Full disclosure of Japanese Patent Application No. 2005-224505 (filed Aug. 2, 2005) and Japanese Patent Application No. 2006-119408 (filed Apr. 24, 2006) including description, claims, drawings and abstract is incorporated hereinto by reference.

BACKGROUND ART

As production methods of L-amino acid, various methods such as extraction procedure, chemical synthetic method, fermentation method, enzymatical synthetic method and the like are known. The extraction procedure requires a large-scale facility for purification of protein hydrolysates. Since amino acid produced by a chemical synthetic method is generally in the form of a racemate, production of an optically active form requires an expensive resolving agent, an asymmetric catalyst and the like. The fermentation method requires a large-scale purification facility as in the extraction procedure since the resulting product has a low concentration, and is unsuitable for the synthesis of non-natural amino acids. The enzymatical synthetic method avoids these problems by utilizing an economical biological catalyst, and can provide an efficient production method at a lower cost.

As an enzymatical synthetic method of L-amino acid, for example, a method including reacting racemic amino acid with D-amino acid oxidase is known.

D-amino acid oxidase (enzyme No. [EC1.4.3.3]) is an enzyme that oxidizes D-amino acid in the presence of oxygen and produces hydrogen peroxide, 2-oxo acid, and ammonia. D-amino acid oxidase is known to have an industrially useful activity such as production of L-amino acid and 2-oxo acid by stereoselective oxidation of racemic amino acid, and the like. In addition, L-amino acid is a useful compound as a synthetic intermediate for pharmaceutical products and the like, and a sweetener.

As microorganisms producing D-amino acid oxidase, for example, *Trigonopsis variabilis* (Patent Reference 1), *Fusarium oxysporum* (Patent Reference 2), *Candida tropicalis* (Non-Patent Reference 1) and the like are known, each of which enzymes was purified and isolated, and the properties thereof have been clarified. In addition, as to the expression of D-amino acid oxidase gene in a transformant, that of genes derived from, for example, *Trigonopsis variabilis* (Patent Reference 3), *Fusarium solani* (Patent Reference 4), *Rhodotorula gracilis* (Patent Reference 5), *Candida boidinii* (Non-patent Reference 2) are known. For high production of D-amino acid oxidase in these transformants, in many cases, a method of highly producing an enzyme, which includes culturing while suppressing expression, and then adding an inducer and the like, is known.

As regards *Candida intermedia* belonging to *Candida* genus, it is known to have a D-amino acid oxidase activity when it is in crude enzyme solution (Non-Patent Reference 3).

Moreover, as an enzymatic synthetic method of L-amino acid, for example, a production method by a stereo inversion reaction, wherein L-amino acid is produced by reacting racemic amino acid with D-amino acid oxidase, amino acid dehydrogenase and an enzyme having a coenzyme-regenerating activity, is known (Non-Patent References 4, 5). However, the methods disclosed in Non-Patent References 4, 5 have problems for industrial application because it requires an expensive commercially available enzyme and a purified enzyme from a microorganism.

To solve this problem, for example, a method comprising preparing and culturing a transformant having respective genes encoding D-amino acid oxidase, amino acid dehydrogenase, an enzyme having coenzyme-regenerating activity, and reacting same with racemic amino acid to give L-amino acid is known (Patent Reference 6). According to the Examples described in Patent Reference 6, however, the concentration of L-amino acid produced by a reaction using the transformant is about 25 mM, which is low for an industrial production.

Patent Reference 1: JP-B-62-501677
Patent Reference 2: JP-A-11-318439
Patent Reference 3: JP-A-63-71180
Patent Reference 4: EP-A-364275
Patent Reference 5: WO97/040171
Patent Reference 6: WO05/090950
Non-Patent Reference 1: "Some Properties of Peroxisome associated D-amino Acid Oxidase from *Candida tropicalis*", Agricul. and Biol. Chemistry, 1986, Vol. 50, No. 10, page 2637
Non-Patent Reference 2: "Characterization and High-level Production of D-Amino Acid Oxidase in *Candida boidinii*", Biosci. Biotechnol. Biochem., 2001, Vol. 65, No. 3, page 627
Non-Patent Reference 3: "Production of D-Amino Acid Oxidase by *Candida tropicalis*", J. Ferment. Technol., 1977, Vol. 55, No. 1, page 13
Non-Patent Reference 4: "Enzymatic Conversion of Racemic Methionine to the L-Enantiomer", J. Chem. Soc. Chem. Commun., 1990, Vol. 13, page 947
Non-Patent Reference 5: "Enzymatic synthesis of chiral intermediates for Omapatrilat, an antihypertensive drug", Biomolecular Engineering, 2001, Vol. 17, page 167

DISCLOSURE OF THE INVENTION

Problems to be Solved by the Invention

D-amino acid oxidase obtained in the present invention is an enzyme that oxidizes D-amino acid in the presence of oxygen, and produces hydrogen peroxide, 2-oxo acid and ammonia. Moreover, it is a useful enzyme utilizable for a stereo inversion reaction by which racemic amino acid is quantitatively converted to L-amino acid via keto acid or imino acid, by using D-amino acid oxidase and amino acid dehydrogenase, or amino acid dehydrogenase and an enzyme having a coenzyme-regenerating activity.

An object of the present invention is to provide novel a D-amino acid oxidase. In addition, an object of the present invention is to clarify the amino acid sequence of the D-amino acid oxidase and the base sequence of the gene, and provide a microorganism or transformant having an ability to produce the enzyme.

In addition, the object of a preferable embodiment of the present invention is to provide a transformant that highly produces D-amino acid oxidase and simultaneously produces amino acid dehydrogenase, and an enzyme having a coenzyme-regenerating activity.

Moreover, the present invention provides an efficient production method of L-amino acid, 2-oxo acid or cyclic imine, which utilizes the above D-amino acid oxidase or the above transformant.

Means of Solving the Problems

In view of the above-mentioned problems, the present inventors isolated and purified D-amino acid oxidase from *Candida intermedia*, achieved isolation of D-amino acid oxidase gene and expression in a host microorganism, and prepared a transformant having high activity. In the case of D-amino acid oxidase obtained in the present invention, high production was possible even when a transformant was cultured without using a means such as suppression of expression, addition of an inducer and the like. By reacting, with the racemic amino acid, D-amino acid oxidase obtained in the present invention, solely or in combination with an amino acid dehydrogenase and an enzyme having a coenzyme-regenerating activity, production of 2-oxo acid or L-amino acid has been enabled, which resulted in the completion of the present invention.

The present inventors have further conducted intensive studies and prepared a transformant having a D-amino acid oxidase gene, and respective genes encoding amino acid dehydrogenase and an enzyme having a coenzyme-regenerating activity. In general, a transformant having plural and different enzyme genes is expected to show decreased production volume of each enzyme, as compared to transformants independently having respective enzyme genes. Surprisingly, however, they have found that, in a preferable embodiment of the present invention, a transformant having a D-amino acid oxidase gene, and genes encoding amino acid dehydrogenase and an enzyme having a coenzyme-regenerating activity shows an increased activity value for one culture medium of D-amino acid oxidase by not less than 50-fold as compared to a transformant having a D-amino acid oxidase gene alone (corresponding to Example 12 mentioned below).

Heretofore, with regard to a transformant having a D-amino acid oxidase gene and one or more genes of polypeptide having a different enzyme activity from that of D-amino acid oxidase (e.g., amino acid dehydrogenase, and coenzyme-regenerating enzyme), an embodiment wherein the activity of D-amino acid oxidase markedly increased as compared to a transformant having a D-amino acid oxidase gene alone is not known. For example, the aforementioned Patent Reference 6 (WO05/090950) does not disclose an embodiment wherein the activity of D-amino acid oxidase of a transformant having genes of D-amino acid oxidase, amino acid dehydrogenase, and an enzyme having a coenzyme-regenerating activity increased as compared to a transformant having a D-amino acid oxidase gene alone.

The fact that the above-mentioned transformant having respective genes shows a remarkably improved D-amino acid oxidase activity as compared to a transformant having a D-amino acid oxidase gene alone was found by a special attempt in the present inventor. Moreover, an efficient production of L-amino acid has become possible by reacting a transformant having genes of D-amino acid oxidase, amino acid dehydrogenase and an enzyme having coenzyme-regenerating activity, which is obtained in a preferable embodiment of the present invention, with racemic amino acid, which resulted in the completion of the present invention.

Accordingly, the present invention has the following one or plural characteristics.

[1] One of the characteristics of the present invention is a polypeptide derived from *Candida intermedia* and having a D-amino acid oxidase activity, which has the following physicochemical properties:
(1) Molecular Weight
molecular weight about 252,000
molecular weight of subunit about 42,000;
(2) Range of Operative Temperature
temperature range at least 20° C.-60° C.;
(3) Range of Operative pH
pH range at least 6-10.5.

[2] One of the characteristics of the present invention is a polypeptide of the following (a), (b) or (c):
(a) a polypeptide having the amino acid sequence shown in Sequence Listing SEQ ID NO: 1;
(b) a polypeptide having an amino acid sequence wherein one or a few amino acids of the amino acid sequence shown in Sequence Listing SEQ ID NO: 1 are substituted, inserted, deleted and/or added, and having a D-amino acid oxidase activity;
(c) a polypeptide having an amino acid sequence having a homology of not less than 69% with the amino acid sequence shown in Sequence Listing SEQ ID NO: 1, and having a D-amino acid oxidase activity.

[3] One of the characteristics of the present invention is a DNA encoding the polypeptide of the aforementioned [1] or [2].

[4] The DNA of preferable embodiments of the present invention is a DNA of the following (d), (e) or (f):
(d) a DNA having a base sequence shown in Sequence Listing SEQ ID NO: 2;
(e) a DNA having a base sequence wherein one or a few bases of the base sequence shown in Sequence Listing SEQ ID NO: 2 are substituted, inserted, deleted and/or added, and encoding a polypeptide having a D-amino acid oxidase activity;
(f) a DNA having a base sequence having a homology of not less than 67% with the base sequence shown in Sequence Listing SEQ ID NO: 2, and encoding a polypeptide having a D-amino acid oxidase activity.

[5] One of the characteristics of the present invention is a recombinant plasmid obtained by inserting the DNA of the aforementioned [3] or [4] into a vector.

[6] The recombinant plasmid of a preferable embodiment of the present invention is a recombinant plasmid wherein a DNA encoding a polypeptide having a different enzyme activity from D-amino acid oxidase is additionally inserted into a vector.

[7] One of the characteristics of the present invention is a transformant obtained by transforming a host microorganism with the recombinant plasmid of the aforementioned [5].

[8] A preferable embodiment of the present invention is the transformant of [7], into which a DNA encoding a polypeptide having an enzyme activity other than that of D-amino acid oxidase has been additionally introduced.

[9] One of the characteristics of the present invention is a method of producing D-amino acid oxidase, comprising culturing a microorganism having an ability to produce the polypeptide of the aforementioned [1] or [2], accumulating the polypeptide in the culture, and recovering same.

[10] One of the characteristics of the present invention is a method of producing L-amino acid represented by the formula (2):

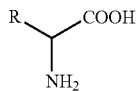 (2)

wherein R represents a C1-20 alkyl group optionally having substituent(s), a C7-20 aralkyl group optionally having substituent(s), or a C6-20 aryl group optionally having substituent(s), or 2-oxo acid represented by the formula (3):

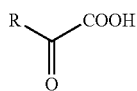 (3)

wherein R represents as defined above, which comprises reacting the polypeptide of the aforementioned [1] or [2], or a microorganism having an ability to produce the polypeptide, with a racemic amino acid represented by the formula (1):

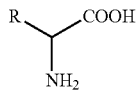 (1)

wherein R represents as defined above.

[11] One of the characteristics of the present invention is a method of producing cyclic L-amino acid represented by the formula (5):

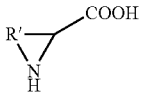 (5)

wherein R' is a C2-7 alkyl chain optionally having substituent(s), or a cyclic imine represented by the formula (6):

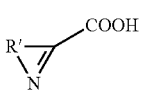 (6)

wherein R' is as defined above, which comprises reacting the polypeptide of [1] or [2], or a microorganism having an ability to produce the polypeptide with a cyclic amino acid represented by the formula (4):

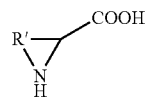 (4)

wherein R' is as defined above.

[12] One of the characteristics of the present invention is a method of producing L-amino acid represented by the formula (2):

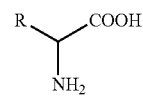 (2)

wherein R represents a C1-20 alkyl group optionally having substituent(s), a C7-20 aralkyl group optionally having substituent(s), or a C6-20 aryl group optionally having substituent(s), which comprises reacting, in the presence of an amino acid dehydrogenase and an enzyme having a coenzyme-regenerating activity, the polypeptide of [1] or [2], or a microorganism having an ability to produce the polypeptide with a racemic amino acid represented by the formula (1):

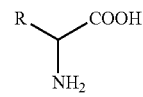 (1)

wherein R represents as defined above.

[13] One of the characteristics of the present invention is a method of producing cyclic L-amino acid represented by the formula (5):

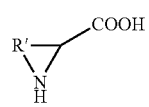 (5)

wherein R' is a C2-7 alkyl chain optionally having substituent(s), which comprises reacting, in the presence of an amino acid dehydrogenase and an enzyme having a coenzyme-regenerating activity, the polypeptide of [1] or [2] or a microorganism having an ability to produce the polypeptide with a cyclic amino acid represented by the formula (4):

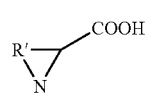 (4)

wherein R' is as defined above.

[14] One of the characteristics of the present invention is a method of increasing a production amount of D-amino acid oxidase, which comprises transforming a host microorganism with a DNA encoding D-amino acid oxidase and a DNA encoding at least one kind of polypeptide having an enzyme activity different from that of the D-amino acid oxidase.

[15] One of the characteristics of the present invention is a recombinant plasmid comprising a DNA encoding a polypeptide having a D-amino acid oxidase activity and a DNA encoding a polypeptide having an enzyme activity different from that of the D-amino acid oxidase as insertion fragments, which plasmid shows an improved production amount of D-amino acid oxidase as compared to a recombinant plasmid containing only a DNA encoding a polypeptide having the aforementioned D-amino acid oxidase activity as an insertion fragment.

[16] One of the characteristics of the present invention is a transformant obtained by transforming a host microorganism with a DNA encoding a polypeptide having a D-amino acid oxidase activity and a DNA encoding a polypeptide having an enzyme activity different from that of the D-amino acid oxidase, which transformant shows an improved D-amino acid oxidase activity as compared to a transformant transformed with only a DNA encoding a polypeptide having the aforementioned D-amino acid oxidase activity.

[17] One of the characteristics of the present invention is a method of producing D-amino acid oxidase, which comprises culturing the transformant of [16], accumulating D-amino acid oxidase in a culture, and recovering same.

[18] One of the characteristics of the present invention is a method of producing the aforementioned L-amino acid represented by the formula (2) or the aforementioned cyclic L-amino acid represented by the formula (5), which comprises reacting the transformant of [16] with the aforementioned racemic amino acid represented by the formula (1) or the aforementioned cyclic amino acid represented by the formula (4).

Other characteristics and the effects thereof of the present invention can be clarified by the following embodiments and drawings.

Effects of the Invention

The present invention has the aforementioned constitution, and can produce novel D-amino acid oxidase efficiently. Moreover, L-amino acid, 2-oxo acid, or cyclic imine can be efficiently produced by utilizing the D-amino acid oxidase, or a transformant or microorganism that produces the D-amino acid oxidase.

In preferable embodiments of the present invention, L-amino acid can be efficiently produced by utilizing a transformant producing D-amino acid oxidase, an amino acid dehydrogenase and an enzyme having a coenzyme-regenerating activity. According to such preferable embodiments, separate cultivation of transformants that produce respective enzymes is not necessary, and technical problems in that a large amount of a culture medium is necessary since the production amount of D-amino acid oxidase becomes insufficient depending on the kind of racemic amino acid as a reaction substrate, and the like can be resolved.

BEST MODE FOR EMBODYING THE INVENTION

Figure 1:
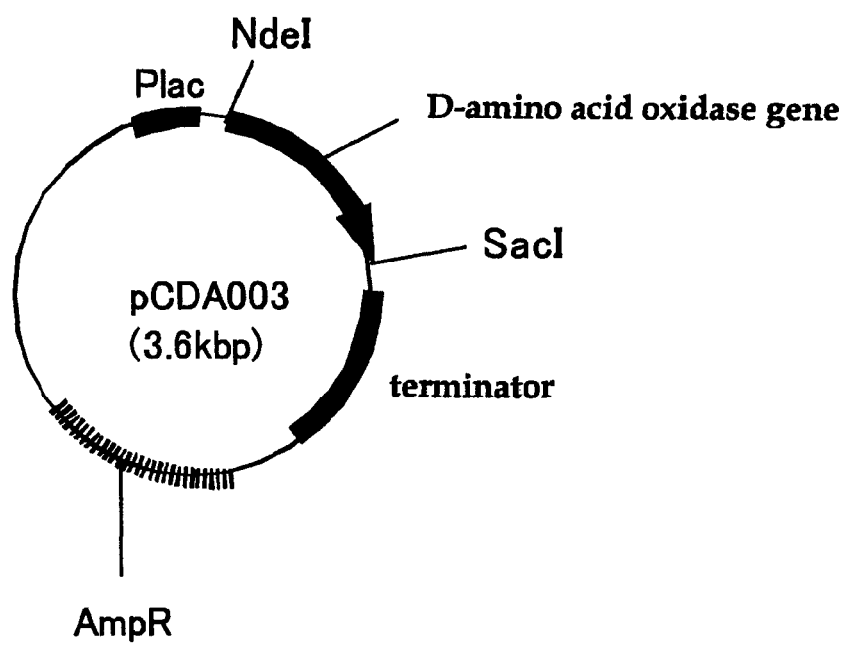
FIG. 1 shows the construction of recombinant plasmid pCDA003 containing a D-amino acid oxidase gene as an embodiment of the present invention.

The present invention is explained in detail in the following by referring to Examples. The scope of the present invention is not limited by the embodiments and Examples.

1. Polypeptide

The polypeptide as an embodiment of the present invention is first explained. The polypeptide as an embodiment has a D-amino acid oxidase activity, and is characterized by the following physicochemical properties.

1) effect

It oxidizes D-amino acid in the presence of oxygen to produce 2-oxo acid, hydrogen peroxide, and ammonia.

2) molecular weight molecular weight about 252,000 molecular weight of subunit about 42,000;

3) Km value relative to D-phenylalanine about 1.7 mM;

4) Range of operative temperature temperature range at least about 20° C.-about 60° C., optimal temperature about 40° C.-about 50° C.;

(The temperature range means a temperature range, in which an enzyme acts preferably, and the optimal temperature means a temperature, at which an enzyme acts most preferably. This enzyme also acts at a temperature other than the above-mentioned temperature range.)

5) Range of operative pH pH range at least about 6-about 10.5, optimal pH about 8.5-about 9.5;

(The pH range means a pH range, in which an enzyme acts preferably, and the optimal pH means a pH, at which an enzyme acts most preferably. This enzyme also acts at a pH other than the above-mentioned pH range.)

6) Temperature stability
   stable at 40° C. or less;
7) pH Stability
   stable at pH 7.8-8.7;
8) Specific activity (the enzyme amount that produces 1 μmol of hydrogen peroxide in 1 min is defined as 1 unit) 44.8 unit (30° C.) per 1 mg of pure enzyme.

The D-amino acid oxidase of the embodiment has, for example, the following different properties as compared to other D-amino acid oxidases.

(a) The optimal temperature and optimal pH thereof are different from those of D-amino acid oxidase of *Fusarium oxysporum* (JP-A-11-318439) having an optimal temperature of 30-40° C. and an optimal pH of 7.5-8.
(b) The enzyme structure is different from that of D-amino acid oxidase of *Trigonopsis variabilis* (JP-B-62-501677, JP-A-63-71180), which is a homo dimer structure consisting of a subunit of molecular weight of 43,000, and the amino acid sequence is also greatly different (amino acid sequence homology 31.6%).
(c) The enzyme structure is different from that of D-amino acid oxidase of *Candida boidinii* (Biosci. Biotechnol. Biochem., 2001, Vol. 65, No. 3, page 627; Yeast, 2000, Vol. 16, page 1217), which is a monomer structure with a molecular weight of 38,000, and the amino acid sequence is also greatly different (amino acid sequence homology 60.1%).
(d) The enzyme structure is different from that of D-amino acid oxidase of *Rhodotorula gracilis* (WO97/040171; Protein expression and purification, 1998, Vol. 14, page 289), which is a homo dimer structure with a molecular weight of 41,000, and the amino acid sequence is also greatly different (amino acid sequence homology 28.9%).
(e) The amino acid sequence is greatly different from that of D-amino acid oxidase of *Fusarium solani* (EP364275) (amino acid sequence homology 29.0%).
(f) The enzyme structure is different from that of D-amino acid oxidase of *Candida tropicalis* (Agricul. and Biol. Chemistry, 1986, vol. 50, No. 10, page 2637), which is a monomer structure with a molecular weight of 39,000.

The "homology" in the embodiment can be determined using a method well known to those of ordinary skill in the art, sequence analysis software and the like. As an example here, the homology search of GENETYX Ver. 7 genetic information processing software/Windows version (manufactured by GENETYX CORPORATION) was used.

2. D-amino Acid Oxidase Activity Assay

In an embodiment, for assay of D-amino acid oxidase activity of polypeptide, hydrogen peroxide produced by the reaction can be quantitatively measured by an enzyme method using peroxidase. Quantitative measurement of hydrogen peroxide is performed by an enzyme method as follows.

An enzyme solution is appropriately diluted, mixed with a chromogenic solution containing 50 mM DL-phenylalanine, 0.80 mM 4-aminoantipyrine, 1.31 mM N-ethyl-N-(2-hydroxy-3-sulfopropyl)-m-toluidine, 6 u/ml peroxidase (manufactured by TOYOBO Inc.), and 50 mM Tris-hydrochloric acid buffer (pH 8.0) at 1:5, and reacted at 30° C. for 30 min. The absorbance at 555 nm is measured, and the amount of hydrogen peroxide produced in the reaction mixture is quantified based on the analytical curve prepared in advance. In the embodiment, unless otherwise specified, this method was used to assay the D-amino acid oxidase activity.

3. Microorganism

The polypeptide of the embodiment can be obtained from a microorganism having a D-amino acid oxidase activity. While the D-amino acid oxidase to be used in the present invention may be derived from animal, plant or microorganism, one derived from a microorganism is preferable for industrial use.

Examples of the microorganism having an ability to produce D-amino acid oxidase include known microorganisms having an ability to produce the enzyme, such as *Arthrobacter*, *Aspergillus*, *Candida*, *Cryptococcus*, *Curvularia*, *Exophiala*, *Fusarium*, *Gibberella*, *Hansenula*, *Kloeckera*, *Kluyveromyces*, *Neurospora*, *Phichia*, *Rhodosporidium*, *Rhodotorula*, *Sporobolomyces*, *Trigonopsis*, *Verticillium*, and *Yarrowia* and the like.

Of these, microorganisms belonging to the genus *Candida*, more preferably *Candida intermedia*, are preferable, and still more preferred is *Candida intermedia* NBRC0761 strain.

The microorganism that produces the polypeptide of the embodiment may be a wild strain of the aforementioned microorganisms, or an improved mutant strain. The mutant strain can be produced by a method well known to those of ordinary skill in the art, such as UV irradiation, or a treatment with a pharmaceutical agent such as N-methyl-N'-nitro-N-nitrosoguanidine (NTG), ethylmethanesulfonate (EMS) and the like.

The medium for cultivation of a microorganism that produces the polypeptide of the present invention is not particularly limited as long as the microorganism can grow. For example, a usual liquid medium containing carbohydrates such as glucose and sucrose, alcohols such as ethanol and glycerol, fatty acids such as oleic acid and stearic acid, or the esters thereof, oils such as canola oil, soybean oil as a carbon source; ammonium sulfate, sodium nitrate, peptone, casamino acid, corn steep liquor, wheat bran, yeast extract and the like as a nitrogen source; magnesium sulfate, sodium chloride, calcium carbonate, dipotassium hydrogen phosphate, potassium dihydrogen phosphate and the like as an inorganic salt; and malt extract, meat extract and the like as other nutrient source can be used.

Moreover, a small amount of a substance that enhances the production of D-amino acid oxidase, such as amino acid or amino acid derivative, can also be added. The concentration of such substance that enhances the production of D-amino acid oxidase in a medium is selected from the range of 0.001 wt %-10 wt %, preferably 0.01 wt %-1 wt %.

The culture is generally carried out aerobically. The temperature is within the range of 10° C.-60° C., preferably 20° C.-50° C., pH is within the range of 3-11, preferably pH 5-9, and the culture time is about one day −5 days. In addition, either a batch culture method or a continuous culture method may be applied.

After the completion of culture, microbial cells are collected from the culture medium by centrifugation and the like, and disrupted by sonication and the like to give a crude enzyme solution. The crude enzyme solution is purified by salting out, column chromatography and the like to give the polypeptide of the present invention.

4. Amino Acid Sequence

The polypeptide of the present invention may be a natural enzyme obtained from a microorganism as mentioned above, or may be a recombinant enzyme produced by genetic recombination techniques. Examples of the natural enzyme include the polypeptide shown by Sequence Listing, SEQ ID NO: 1.

In addition, the polypeptide as an embodiment of the present invention may be a polypeptide having an amino acid sequence wherein one or a few amino acids of the amino acid sequence shown in Sequence Listing SEQ ID NO: 1 are substituted, inserted, deleted and/or added, and having a D-amino acid oxidase activity; or may be a polypeptide having an amino acid sequence having a homology of not less than 69%, preferably not less than 70%, not less than 75%, not less than 80%, not less than 85%, not less than 90%, not less than 95%, more preferably not less than 99%, with the amino acid sequence shown by SEQ ID NO: 1, and having a D-amino acid oxidase activity.

While the number of amino acids in "a few amino acids" is not limited as long as the D-amino acid oxidase activity is not lost, it is preferably not more than 20 amino acids, more preferably not more than 15 amino acids, more preferably not more than 10 amino acids, and most preferably 5, 4, 3, or 2 or lower.

In addition, "polypeptide having a D-amino acid oxidase activity" means a polypeptide showing not less than 10%, preferably not less than 40%, more preferably not less than 60%, still more preferably not less than 80%, of the activity afforded by a polypeptide consisting of the amino acid sequence shown in SEQ ID NO: 1 when it is used under the above-mentioned activity assay conditions.

5. DNA

The "DNA" as an embodiment of the present invention is explained. The DNA of the present invention only needs to be a DNA encoding the above-mentioned polypeptide. It may be a DNA shown by Sequence Listing SEQ ID NO: 2, a DNA having a base sequence wherein one or a few bases of the base sequence shown in Sequence Listing SEQ ID NO: 2 are substituted, inserted, deleted and/or added and encoding a polypeptide having a D-amino acid oxidase activity.

While the number of bases in "a few bases" is not limited as long as a polypeptide encoded by the DNA does not lose the D-amino acid oxidase activity, it is preferably not more than 50 bases, more preferably not more than 30 bases, more preferably not more than 20 bases, and most preferably 10, 9, 8, 7, 6, 5, 4, 3, or 2 or lower.

In addition, it may be a DNA having a base sequence having a homology of not less than 67%, preferably not less than 70%, not less than 75%, not less than 80%, not less than 85%, not less than 90%, not less than 95%, more preferably not less than 99%, with the base sequence shown in Sequence Listing SEQ ID NO: 2, and encoding a polypeptide having a D-amino acid oxidase activity.

Moreover, the DNA of the present invention may be a DNA that hybridizes to a DNA consisting of a base sequence complementary to the base sequence shown in Sequence Listing SEQ ID NO: 2 under stringent conditions, and encoding a polypeptide having a D-amino acid oxidase activity.

As used herein, by the "DNA that hybridizes to a DNA consisting of a base sequence complementary to the base sequence shown in Sequence Listing SEQ ID NO: 2 under stringent conditions" refers to a DNA capable of specifically forming a hybrid with a DNA having a base sequence complementary to the base sequence shown in Sequence Listing SEQ ID NO: 2, when colony hybridization method, plaque hybridization method, Southern hybridization method and the like are performed.

As used herein, the stringent conditions refer to those under which, for example, hybridization in an aqueous solution having a composition of 75 mM trisodium citrate, 750 mM sodium chloride, 0.5% dodecyl sodium sulfate, 0.1% bovine serum albumin, 0.1% polyvinylpyrrolidone, and 0.1% Ficoll 400 (manufactured by Amersham Bioscience Co.) at 65° C. and then washing with an aqueous solution having a composition of 15 mM trisodium citrate, 150 mM sodium chloride and 0.1% dodecyl sodium sulfate at 60° C. are performed. Preferably, they refer to the conditions under which washing with an aqueous solution having a composition of 15 mM trisodium citrate, 150 mM sodium chloride and 0.1% dodecyl sodium sulfate is performed at 65° C., after hybridization under the above-mentioned condition, more preferably, washing with an aqueous solution having a composition of 1.5 mM trisodium citrate, 15 mM sodium chloride and 0.1% dodecyl sodium sulfate is performed at 65° C., after hybridization under the above-mentioned conditions.

The DNA (D-amino acid oxidase gene) of the present invention can be obtained from the aforementioned microorganisms having a D-amino acid oxidase activity. To obtain the DNA of interest, for example, the following method can be employed.

First, D-amino acid oxidase purified by a microorganism having a D-amino acid oxidase activity is reacted with a protease such as lysylendopeptidase and the like to digest to a polypeptide having a suitable size, and then the obtained polypeptide is purified by HPLC and the like, and the internal amino acid sequence is determined by a vapor phase protein sequencer and the like. Then, DNA primers designed based on the homologous sequence region in known D-amino acid oxidases are synthesized.

Then, a chromosomal DNA is isolated from a microorganism to be the origin of the D-amino acid oxidase. The chromosomal DNA can be obtained from a cultured cell using an UltraClean Microbial DNA Isolation Kit (manufactured by MO BIO Laboratories, Inc.) and the like. The object gene can be partly obtained by PCR using the chromosomal DNA as a template and the above-mentioned DNA primers.

Next, DNA fragments encoding the N-terminal side and the C-terminal side of the obtained partial gene can be obtained by inverse PCR (see, for example, Nucleic Acids Res., 16, 8186 (1988)). The base sequences of the DNA fragments are determined, and combined with the base sequence of the partial gene to give a full-length base sequence of the D-amino acid oxidase gene, which is assumed to contain from the translation initiation site to the stop codon.

When the presence of intron in the D-amino acid oxidase gene obtained from chromosomal DNA is presumed by the analysis of the obtained base sequence, a D-amino acid oxidase gene, from which the intron is removed by the method shown below, can be obtained.

First, a microorganism to be the origin of D-amino acid oxidase is cultured to obtain microbial cells, and the total RNA is extracted from the obtained microbial cells using ISOGEN (manufactured by NIPPON GENE CO.), and a complementary strand DNA (cDNA) is prepared using TaKaRa RNA LA PCR Kit (AMV) Ver. 1.1 (manufactured by TaKaRa) and the total RNA as a template. Primers are designed from the base sequences of the N-terminal part and C-terminal part of the above-mentioned D-amino acid oxidase gene full-length sequence obtained by inverse PCR method. PCR is performed using the designed primer and using cDNA as a template, and open reading frame is determined from the full-length sequence free of the intron. It can be confirmed that the amino acid sequences encoded by the determined open reading frame contain the above internal amino acid sequences of the D-amino acid oxidase.

6. Transformant and Vector

The DNA obtained by the above-mentioned method, or a recombinant plasmid obtained by incorporating the above DNA into a vector is used to transform a host microorganism to give a transformant.

As the host and vector, the host vector system described in "Recombinant DNA Experiment Guidances" (ed. Science Technology Agency Research and Development Bureau Life Sciences Division: revised Mar. 22, 1996) can be used. For example, as the host, microorganisms belonging to the genera *Escherichia, Pseudomonas, Flavobacterium, Bacillus, Ser-*

*ratia, Corynebacterium, Brevibacterium, Agrobacterium, Acetobacter, Gluconobacter, Lactobacillus, Streptococcus,* and *Streptomyces* can be used.

As a vector, a plasmid, a phage, or a derivative thereof derived from microorganisms, which is capable of autonomously replicating in the above-mentioned host, can be used. Among these, *Escherichia coli* is preferably used as the host microorganism, and a vector capable of autonomous replication in the microorganism is preferably used as the vector. Examples of such vector include pUC18, pUC19, pBR322, pACYC184, pSTV28, pSTV29, pSC101, pT7Blue or pUCNT, or derivatives thereof. The derivatives thereof refers to one having modification in promoter, terminator, enhancer, SD sequence, the origin site of replication (ori), other genes involved in regulation, or the like, for the purpose of increasing the production amount of the enzyme and stabilization of the plasmid, or one having modified drug resistance, one modified restriction enzyme site of cloning site and the like.

As one example of transformant, using recombinant plasmid pCDA003 in which a DNA obtained from *Candida intermedia* NBRC0761 strain in the manner mentioned above is incorporated into pUCNT (see WO94/03613), *Escherichia coli* HB101 and JM109 are transformed, whereby transformant *Escherichia coli* HB101 (pCDA003) and JM109 (pCDA003) can be obtained.

The transformant *Escherichia coli* HB101 (pCDA003) obtained in the present invention was deposited on Jul. 10, 2006 under a receipt number FERM BP-10639 (domestic deposit strain originally deposited on Jul. 19, 2005 was transferred to an international deposit based on the Budapest Treaty), and the transformant *Escherichia coli JM*109 (pCDA003) was deposited on Jul. 10, 2006 under a receipt number FERM BP-10638 at the National Institute of Advanced Industrial Science and Technology the International Patent Organism Depositary (IPOD: 1-1, Tsukuba-shi Higashi 1-chome, Ibaragi-ken, 305-8566) (domestic deposit strain originally deposited on Jun. 28, 2005 was transferred to an international deposit based on the Budapest Treaty).

The recombinant DNA technique used in the present invention is well known in the art and described, for example, in Molecular Cloning 2nd Edition (Cold Spring Harbor Laboratory Press, 1989), Current Protocols in Molecular Biology (Greene Publishing Associates and Wiley-Interscience).

7. Culture of Transformants

By culturing the above-mentioned transformants capable of producing the D-amino acid oxidase of the present invention, the enzyme can be produced in a large amount, which can be utilized for the production of L-amino acid or 2-oxo acid.

For culture of a microorganism, a usual medium can be used. The medium to be used for the culture can be a usual medium containing nutrients such as a carbon source, a nitrogen source, inorganic salts and the like. When trace amounts of organic nutrients such as vitamin and amino acid are added, preferable results can often be obtained. As the carbon source, carbohydrates such as glucose and sucrose, organic acids such as acetic acid and alcohols can be used as appropriate. As the nitrogen source, ammonium salt, aqueous ammonia, ammonia gas, urea, yeast extract, peptone, corn steep liquor and the like can be used. As the inorganic salt, phosphate, magnesium salt, potassium salt, sodium salt, calcium salt, iron salt, sulfate, chlorine and the like can be used.

The culture can be performed in a temperature range of from 25° C. to 40° C., particularly preferably from 25° C. to 37° C. In addition, culture can be performed at pH 4 to 8, particularly preferably pH 5 to 7.5. Furthermore, either a batch culture method or a continuous method can be used.

Treatments for inducing the enzyme, such as addition of isopropyl-1-thio-β-D-galactoside (IPTG) or lactose, can also be carried out, as necessary.

8. Production Method of L-amino Acids and the Like

An efficient production method of L-amino acid, t-oxo acid, or cyclic imine by the use of D-amino acid oxidase obtained in the embodiment is explained. 2-oxo acid can be obtained by reacting racemic amino acid with D-amino acid oxidase to oxidize D-amino acid (optical resolution reaction). In this reaction, it is assumed that imino acid is produced as an intermediate from D-amino acid to 2-oxo acid. However, imino acid is soon converted to 2-oxo acid by hydrolysis and 2-oxo acid alone is finally obtained. Cyclic imine can be obtained by reacting cyclic amino acid with D-amino acid oxidase. L-amino acid can be obtained as a residual substrate of the aforementioned resolution reaction, and can also be converted to L-amino acid by further bringing 2-oxo acid, imino acid or cyclic imine produced by the aforementioned reaction into contact with amino acid dehydrogenase to stereo inversion reaction.

9. Amino Acid Dehydrogenase

Here, amino acid dehydrogenase is an enzyme having an activity to reductively aminate 2-oxo acid or cyclic imine in the presence of ammonia. Examples thereof include phenylalanine dehydrogenase, leucine dehydrogenase and pyrroline-2-carboxylic acid reductase.

As the amino acid dehydrogenase to be used in the present invention, one derived from animal, plant or microorganism can be used. For industrial use, one derived from microorganism is preferable.

As the microorganism, any can be used as long as it has an ability to produce the enzyme. Examples thereof include *Brevibacterium, Rhodococcus, Sporosarcina, Thermoactinomyces, Microbacterium, Halomona, Clostridium, Bacillus, Neurospora, Escherichia, Aerobactor* and the like, which are known microorganisms having an ability to produce the enzyme.

Preferable examples thereof include enzymes derived from a microorganism belonging to the genus *Bacillus*. More preferable example includes an enzyme derived from *Bacillus badius* IAM11059 or *Bacillus sphaericus* NBRC3341. *Bacillus badius* IAM11059 is a microorganism that produces phenylalanine dehydrogenase, and known from European Patent No. EP256514 and Bisci. Biotechnol. Biochem., 1995, Vol. 59, number 10, page 1994. Furthermore, *Bacillus sphaericus* NBRC3341 is a microorganism that produces leucine dehydrogenase. It has the same number of amino acid residues as that of known leucine dehydrogenase of *Bacillus subtilis*, and 100% identity in the amino acid sequence. In the gene sequence, 14 bases out of 1095 bases are different. The gene sequence of *Bacillus subtilis* is known from Nature, 1997, Vol. 390, page 249 and NCBI database accession No. CAB14339. Moreover, that pyrroline-2-carboxylic acid reductase is produced by microorganisms belonging to the genera *Neurospora, Escherichia, Aerobactor* is mentioned in Methods Enzymol., 1962, Vol. 5, page 882.

To obtain a highly active strain that highly produces amino acid dehydrogenase efficiently, preparation of a transformed microorganism is effective as known well. The preparation method therefor includes, for example, cloning an amino acid dehydrogenase gene from a strain showing an amino acid dehydrogenase activity, producing a recombinant plasmid with a suitable vector, and transforming a suitable host strain using this plasmid. In addition, the recombinant DNA technique is well known in the art.

10. Coenzyme-regenerating System (Enzyme Having Coenzyme-regenerating Activity)

The above-mentioned reaction by amino acid dehydrogenase requires a reduced form of coenzyme such as NADH, where the coenzyme NADH is converted to an oxidized form with the progress of the reaction. The amount of a coenzyme to be used can be drastically reduced by carrying out the reaction using D-amino acid oxidase and amino acid dehydrogenase in the co-presence of an enzyme having an ability to convert an oxidized form of coenzyme to a reduced form (hereinafter to be referred to as coenzyme-regenerating activity) and a compound to be the substrate of the enzyme.

As the polypeptide having a coenzyme-regenerating activity, for example, hydrogenase, formate dehydrogenase, alcohol dehydrogenase, aldehyde dehydrogenase, glucose-6-phosphate dehydrogenase, glucose dehydrogenase and the like can be used.

Preferably, formate dehydrogenase can be used. As the formate dehydrogenase, one derived from plant or microorganism can be used and, for industrial use, one derived from a microorganism is preferable. As the microorganism, any microorganism can be used as long as it has an ability to produce the enzyme. Examples thereof include the following known microorganisms having an ability to produce the enzyme, such as the genera *Candida, Kloeckera, Pichia, Lipomyces, Pseudomonas, Moraxella, Hyphomicrobium, Paracoccus, Thiobacillus, Ancylobacter.*

Preferable examples thereof include enzymes derived from the microorganisms belonging to the genera *Thiobacillus* and *Ancylobacter*. More preferable examples thereof include enzymes derived from *Thiobacillus* sp. KNK65MA (FERM BP-7671) and *Ancylobacter aquaticus* KNK607M strain (FERM BP-7335).

To obtain a highly active strain that highly produces formate dehydrogenase efficiently, preparation of a transformed microorganism is effective as known well. The preparation method therefor includes, for example, as described in WO03/031626, cloning a formate dehydrogenase gene from a strain showing a formate dehydrogenase activity, producing a recombinant plasmid with a suitable vector, and transforming a suitable host strain using this plasmid. The recombinant DNA technique is well known in the art.

Examples of the transformant thus obtained that highly produces formate dehydrogenase include *Escherichia coli* HB101 (pFT001) (FERM BP-7672) or *Escherichia coli* HB101 (pFT002) (FERM BP-7673) containing formate dehydrogenase gene derived from *Thiobacillus* sp. KNK65MA (FERM BP-7671) described in WO03/031626, and *Escherichia coli* HB101 (pFA001) (FERM BP-7334) containing formate dehydrogenase gene derived from *Ancylobacter aquaticus* KNK607M strain (FERM BP-7335) described in WO02/46427.

For production of amino acid dehydrogenase, formate dehydrogenase by these transformants, production of amino acid dehydrogenase by the aforementioned strains showing an amino acid dehydrogenase activity, or production of formate dehydrogenase by a strain showing a formate dehydrogenase activity, culture only needs to be performed using, for example, a general nutritive medium described in WO03/031626. Where necessary, a treatment for enzyme induction can also be performed.

11. Addition of Catalase

Catalase may be added to a D-amino acid oxidase reaction. Even when catalase is not added, the reaction proceeds and the resulting product can be obtained. However, the yield may decrease due to hydrogen peroxide produced by a D-amino acid oxidase reaction, which degrades a substrate or a resulting product. Addition of catalase suppresses degradation of a substrate or a resulting product, and is expected to increase the yield. Catalase is an enzyme that catalyzes a reaction to degrade hydrogen peroxide into water and oxygen.

As the catalase, one derived from animal, plant or microorganism can be used and, for industrial use, one derived from a microorganism is preferable. As the microorganism, any microorganism can be used as long as it has an ability to produce the enzyme. Examples thereof include the following known microorganisms having an ability to produce the enzyme, such as the genera *Micrococcus, Rhodopseudomonas* and the like. In addition, commercially available enzymes can also be used. Examples of the commercially available enzyme include Catazyme 25L (manufactured by Novozyme) and CATALASE (Beef Liver) (manufactured by P-L Biochemcals, Inc.)

12. Variations of Transformants

D-amino acid oxidase, amino acid dehydrogenase, an enzyme having a coenzyme-regenerating activity and catalase to be used in the present invention may be produced by preparing and culturing transformants introducing each enzyme gene, or preparing and culturing a transformant introducing plural enzyme genes.

In the present invention, each of the produced D-amino acid oxidase, amino acid dehydrogenase, enzyme having a coenzyme-regenerating activity, and catalase can be used as an enzyme itself, and can also be used as a microorganism or a treated product thereof. Here, the treated product of microorganism means, for example, crude extract, freeze-dried organism of cultivated microbial cell, acetone dried organism, or disrupted product of them.

Furthermore, they can be used as an immobilized enzyme obtained by immobilizing an enzyme itself or microbial cells by a known method. For immobilization, crosslinking method, covalent bonding method, physical adsorption method, inclusion method and the like, which are known methods for those of ordinary skill in the art, can be performed.

To obtain a highly active strain that highly produces the above-mentioned D-amino acid oxidase, amino acid dehydrogenase, and an enzyme having a coenzyme-regenerating activity efficiently, as a preferable embodiment of the present invention, preparation of a transformed microorganism is effective as known well. As a preparation method, taking D-amino acid oxidase as an example, D-amino acid oxidase gene is cloned from a strain showing the same activity, a recombinant plasmid with a suitable vector is formed and a host microorganism such as *Escherichia coli* and the like, though not particularly limited, is transformed using the plasmid, according to the method shown in the below-mentioned Examples and the like, whereby a transformant can be obtained.

Furthermore, by preparing a transformant having plural enzyme genes, each enzyme can be produced by the one microbial cell. As a method of preparing a transformant having plural enzyme genes, a method including transforming a recombinant plasmid wherein plural enzyme genes are inserted into the same vector, a method including inserting respective enzyme genes into different vectors having different replication origin (ori) and different drug resistance genes, and transforming the obtained plural recombinant plasmids by the same host microorganism and the like can be mentioned.

According to the above-mentioned method, a transformant having a D-amino acid oxidase gene, and genes of amino acid dehydrogenase and an enzyme having a coenzyme-regenerating activity can be prepared, which shows an activity value that has increased 1.3-fold or above, 2-fold or above, 10-fold or above, moreover, 50-fold or above, per a culture medium of D-amino acid oxidase, as compared to a transformant having a D-amino acid oxidase gene alone (corresponding to the below-mentioned Example 12).

As the vector, the vectors exemplified for D-amino acid oxidase gene in the aforementioned "6. Transformant and vector" can be used in the same manner.

13. Production of L-amino Acids and the Like

Production of L-amino acids, 2-oxo acids or cyclic imines by optical resolution reaction in the present invention, and production of L-amino acids by a stereo inversion reaction in the present invention can be performed by the following methods.

In the aforementioned racemic amino acid represented by the formula (1), as the substrate for both enzyme reactions, R represents C1-20 alkyl group optionally having substituent(s), C7-20 aralkyl group optionally having substituent(s), or C6-20 aryl group optionally having substituent(s). The C1-20 alkyl group optionally having substituent(s) for the above-mentioned R represents not particularly limited and, for example, methyl group, isopropyl group, isobutyl group, 1-methylpropyl group, carbamoylmethyl group, 2-carbamoylethyl group, hydroxymethyl group, 1-hydroxyethyl group, mercaptomethyl group, 2-methylthioethyl group, (1-mercapto-1-methyl) ethyl group, 4-aminobutyl group, 3-guanidinopropyl group, 4(5)-imidazolemethyl group, ethyl group, n-propyl group, n-butyl group, t-butyl group, chloromethyl group, methoxymethyl group, 2-hydroxyethyl group, 3-aminopropyl group, 2-cyanoethyl group, 3-cyanopropyl group, 4-(benzoylamino)butyl group, 2-methoxycarbonylethyl group, and the like can be mentioned.

The C7-20 aralkyl group optionally having substituent(s) is not particularly limited and, for example, benzyl group, indolylmethyl group, 4-hydroxybenzyl group, 2-fluorobenzyl group, 3-fluorobenzyl group, 4-fluorobenzyl group, 3,4-methylenedioxybenzyl group and the like can be mentioned. Examples of the C6-20 aryl group optionally having substituent(s) include phenyl group, 4-hydroxyphenyl group and the like. Examples of the substituent include amino group, hydroxyl group, nitro group, cyano group, carboxyl group, alkyl group, aralkyl group, aryl group, alkanoyl group, alkenyl group, alkynyl group, alkoxyl group, halogen atom and the like.

In addition, in the aforementioned cyclic amino acid represented by the formula (4), R' is C2-7 alkyl chain optionally having substituent(s). Examples of the substituent include amino group, hydroxyl group, nitro group, cyano group, carboxyl group, alkyl group, aralkyl group, aryl group, alkanoyl group, alkenyl group, alkynyl group, alkoxyl group, halogen atom and the like.

14. Optical Resolution Reaction

For a resolution reaction, the above-mentioned substrate is reacted with the aforementioned D-amino acid oxidase in an aqueous solvent. Catalase may be added to the above-mentioned reaction. Catalase degrades hydrogen peroxide produced by the reaction with D-amino acid oxidase and suppresses degradation of a substrate or a resulting product. In addition, FAD may be added to the reaction. FAD is a coenzyme of D-amino acid oxidase and addition thereof is expected to increase the reaction efficiency. The addition concentration of FAD is preferably 0 equivalent amount or above and 10 equivalent amount or below, more preferably 0 equivalent amount or above and 1 equivalent amount or below, more preferably 0 equivalent amount or above and 0.1 equivalent amount or below, relative to the substrate.

15. Stereo Inversion Reaction

In the stereo inversion reaction, the reaction is performed in an aqueous medium in the presence of the above-mentioned substrate, the aforementioned D-amino acid oxidase, the aforementioned amino acid dehydrogenase and an enzyme having a coenzyme-regenerating activity with a compound to be its substrate. Catalase may be added to the reaction. Catalase degrades hydrogen peroxide produced by the reaction of D-amino acid oxidase and suppresses degradation of a substrate or a resulting product.

In addition, FAD may be added to the above-mentioned reaction. FAD is a coenzyme of D-amino acid oxidase and addition thereof is expected to increase the reaction efficiency. The concentration of FAD to be added is preferably 0 equivalent or above and 10 equivalents or below, more preferably 0 equivalent or above and 1 equivalent or below, more preferably 0 equivalent or above and 0.1 equivalents or below, relative to the substrate.

In addition, a coenzyme such as NAD may be added to the above-mentioned stereo inversion reaction. Even when a coenzyme such as NAD is not added, the reaction may proceed due to a coenzyme such as NAD present in a microorganism. However, addition of a coenzyme such as NAD is expected to increase the reaction efficiency. The concentration of a coenzyme such as NAD to be added is preferably 0 equivalent or above and 2 equivalents or below, more preferably 0.00001 equivalents or above and 0.1 equivalents or below, more preferably 0.0001 equivalents or above and 0.01 equivalents or below, relative to the substrate. Whilse the upper limit of the amount of the coenzyme to be added is not particularly limited, it is generally 2 equivalents or below, preferably 0.1 equivalents or below, more preferably 0.01 equivalents or below, from the economical aspects.

Furthermore, ammonia or a salt thereof may be added to the above-mentioned stereo inversion reaction. The concentration of ammonia to be added is preferably 0 equivalent or above and 10 equivalents or below, more preferably 0 equivalent or above and 2 equivalents or below, more preferably 0.1 equivalents or above and 1.5 equivalents or below, relative to the substrate.

The concentration of the substrate charged for the above-mentioned optical resolution and stereo inversion reaction is 0.1% (w/v) or above and 90% (w/v) or below, preferably 1% (w/v) or above and 60% (w/v) or below, and the reactions are performed in a dissolution or suspension state, in which the reaction temperature in the above-mentioned resolution reaction and stereo inversion reaction is controlled to a suitable temperature of 10° C. or above and 80° C. or below, preferably 20° C. or above and 60° C. or below, and the reaction mixture is stood or stirred for some time while keeping the pH at not less than pH 4 and not more than 12, preferably not less than pH 6 and not more than 11. In addition, the substrate may be added at once, or added by portions or continuously. The above-mentioned resolution reaction and stereo inversion reaction may be performed by a batch method or a continuous method.

The resolution reaction and stereo inversion reaction in the present invention can be performed using an immobilized enzyme, a membrane reactor and the like. As the aqueous medium, suitable solvents such as water, buffer, an aqueous medium containing a water-soluble organic solvent such as ethanol, a bilayer system with an aqueous medium containing a hardly water-soluble organic solvent such as ethyl acetate, butyl acetate, toluene, chloroform, n-hexane and the like can be used. Furthermore, antioxidant, surfactant, coenzyme, metal and the like can also be added where necessary.

16. Variation of Stereo Inversion Reaction

Next, as a more preferable embodiment of a stereo inversion reaction, a production method of L-amino acid from a racemic amino acid, which uses D-amino acid oxidase, amino acid dehydrogenase and an enzyme having a coenzyme-regenerating activity is explained. In this embodiment, a reaction is performed in an aqueous medium in the presence of a racemic amino acid, the aforementioned D-amino acid oxidase, amino acid dehydrogenase, an enzyme having a coenzyme-regenerating activity with a compound to be a substrate thereof.

In this embodiment, catalase may also be added. As the catalase, those recited in the aforementioned "11. Catalase" can be used.

In the present invention, each of D-amino acid oxidase, amino acid dehydrogenase, and enzyme having a coenzyme-regenerating activity, which are produced by cultivating a transformant, can be used as an enzyme itself, and can also be used as a transformant or a treated product thereof. Here, the treated product of transformant means, for example, crude extract, freeze-dried organism of cultivated microbial cells, acetone dried organism, or a disrupted product of them.

When a transformant introducing the genes of D-amino acid oxidase, amino acid dehydrogenase, and an enzyme having a coenzyme-regenerating activity in the present invention is used for an enzyme reaction, microbial cells obtained by culturing is used undisrupted, whereby reaction yield can be improved and/or the reaction time can be shortened (corresponding to the below-mentioned Examples 13 and 14).

The concept of the "undisrupted" or "using microbial cells without disruption" includes not only the absence of a physical or chemical treatment is applied to the microbial cells but also the presence of a treatment (e.g., drying treatment, freeze treatment, freeze-dry treatment, acetone drying treatment, or addition of toluene, surfactant and the like) well known to those of ordinary skill in the art, which aims at increasing the cell membrane permeability of the microbial cells.

Furthermore, each enzyme can be used as an immobilized enzyme obtained by immobilizing an enzyme itself or microbial cells by a known method. For immobilization, crosslinking method, covalent bonding method, physical adsorption method, inclusion method and the like, which are known methods for those of ordinary skill in the art, can be performed.

In addition, FAD and/or NAD and the like may be added to the above-mentioned reaction. The amount of FAD, NAD and the like to be added is as indicated above.

Furthermore, ammonia or a salt thereof may be added to the above-mentioned stereo inversion reaction. The concentration of ammonia to be added is preferably 0 equivalent or above and 10 equivalents or below, more preferably 0.3 equivalents or above and 2 equivalents or below, more preferably 0.8 equivalents or above and 1.5 equivalents or below, relative to the substrate.

In this embodiment, racemic amino acid represented by the aforementioned formula (1) and cyclic amino acid represented by the formula (4) can be used as a substrate, wherein the conditions such as concentration of the substrate charged, reaction temperature, reaction pH and the like are also as indicated above.

17. Isolation of Resulting Product

For isolation of L-amino acid, 2-oxo acid or cyclic imine thus produced, they can be separated and purified by a conventional separation method, for example, separation methods of extraction, concentration, crystallization, column chromatography and the like, or a combination thereof.

EXAMPLES

A list of the Examples and Reference Examples is as follows.

Example 1: Isolation and purification of D-amino acid oxidase

Example 2: Properties of D-amino acid oxidase

Example 3: Determination of internal amino acid sequence of D-amino acid oxidase Example 4: Isolation of D-amino acid oxidase gene Example 5: Preparation of Recombinant Plasmid Expressing D-amino acid oxidase gene Example 6: Preparation of Transformant Using Recombinant DNA containing D-amino acid oxidase gene Example 7: Synthesis of L-amino acid or 2-oxo acid by resolution reaction using purified D-amino acid oxidase Example 8: Synthesis of L-amino acid by resolution reaction using strain having D-amino acid oxidase activity Example 9: Synthesis of L-amino acid or 2-oxo acid by resolution reaction using transformant
(1) Synthesis of L-phenylalanine and phenylpyruvic acid from DL-phenylalanine
(2) Synthesis of L-phenylalanine and phenylpyruvic acid from DL-phenylalanine
(3) Synthesis of L-4-fluoro-phenylalanine from DL-4-fluoro-phenylalanine
(4) Synthesis of L-Norvaline and 2-oxovaleric acid from DL-Norvaline
(5) Synthesis of β-chloro-L-alanine from β-chloro-DL-alanine Example 10: Synthesis of L-amino acid using transformant
(1) Synthesis of L-phenylalanine from DL-phenylalanine
(2) Synthesis of L-phenylalanine from DL-phenylalanine
(3) Synthesis of L-4-fluoro-phenylalanine from DL-4-fluoro-phenylalanine
(4) Synthesis of L-Norvaline from DL-Norvaline
(5) Synthesis of L-leucine from DL-leucine Reference Example 1: Preparation of Transformant Having phenylalanine dehydrogenase activity Reference Example 2: Preparation of Transformant Having leucine dehydrogenase activity Example 11: Preparation of Transformant Having D-Amino acid oxidase activity, amino acid dehydrogenase activity and activity of an enzyme having coenzyme-regenerating ability
[1] Preparation of transformant having D-amino acid oxidase, leucine dehydrogenase and formate dehydrogenase activities
[2] Preparation of transformant having D-amino acid oxidase, leucine dehydrogenase and formate dehydrogenase activities
[3] Preparation of transformant having D-amino acid oxidase, phenylalanine dehydrogenase and formate dehydrogenase activities
[4] Preparation of transformant having D-amino acid oxidase, phenylalanine dehydrogenase and formate dehydrogenase activities Example 12: Production of D-amino acid oxidase using transformant Example 13: Synthesis of L-Norvaline using transformant having D-amino acid oxidase, leucine dehydrogenase and formate dehydrogenase activities Example 14: Synthesis of L-tert-leucine using transformant having D-amino acid oxidase, leucine dehydrogenase and formate dehydrogenase activities Comparative Example 1: Synthesis of L-Norvaline using transformant having D-amino acid oxidase activity, and transformant having leucine dehydrogenase and formate dehydrogenase activities Reference Example 3: Preparation of Transformant Having formate dehydrogenase activity Reference Example 4: Preparation of transformant having leucine dehydrogenase activity, and formate dehydrogenase activity Reference Example 5: Preparation of Transformant Having phenylalanine dehydrogenase activity, and formate dehydrogenase activity Reference Example 6: Preparation of Transformant Having D-amino acid oxidase activity Specific examples of the present invention are given below. However, the present invention is not limited to these examples.

Example 1

Isolation and Purification of D-amino Acid Oxidase

*Candida intermedia* NBRC0761 strain was inoculated into 6 ml of a sterilized medium (glucose 1.65%, $NH_4H_2PO_4$ 0.5%, $KH_2PO_4$ 0.25%, $MgSO_4$ 0.1%, $FeCl_3 \cdot 6H_2O$ 0.002%, corn steep liquor 0.1%, pH 5.2 before sterilization) in test tube and aerobically cultured with shaking at 30° C. for 12 hr. 4 ml of this culture solution was inoculated into 400 ml of a sterilized medium (sucrose 1.65%, $NH_4H_2PO_4$ 0.5%, $KH_2PO_4$ 0.25%, $MgSO_4$ 0.1%, $FeCl_3 \cdot 6H_2O$ 0.002%, corn steep liquor 0.1%, FAD 0.0005%, D-alanine 0.089%, pH 5.2 before sterilization, FAD and D-alanine were separately added after sterilization by filtration with a 0.02 µm filter) in a 2 L Sakaguchi flask and aerobically cultured with shaking at 25° C. for 22 hr.

After completion of the culture, microbial cells were harvested by centrifugation, suspended in 50 mM Tris(tris(hydroxymethyl)aminomethane)-hydrochloric acid buffer (pH 8.0), disrupted by sonication, and centrifuged. Ammonium sulfate was added to the supernatant, resulting in a concentration of saturated solution of 40-60%, and the generated precipitate was then obtained by centrifugation. This fraction was dissolved in 50 mM Tris-hydrochloric acid buffer (pH 8.0), dialyzed in the same buffer, applied to DEAE-TOYO-PEAL (manufactured by Tosoh Corporation) for column chromatography, washed with the same buffer, and eluted with the same buffer with the concentration gradient from 0 M to 0.4 M sodium chloride to collect an active fraction. Ammonium sulfate was dissolved in this active fraction to a final concentration of 1 M, and the mixture was applied to Phenyl-TOYOPEAL (manufactured by Tosoh Corporation) for column chromatography and eluted with 50 mM Tris-hydrochloric acid buffer (pH 8.0) with the concentration gradient from 1 M to 0 M ammonium sulfate. The active fraction thus obtained was subjected to column chromatography using 6 ml of RESOURCE Q (manufactured by Amersham Pharmacia Biotech), washed with 50 mM Tris-hydrochloric acid buffer (pH 8.0), and eluted with the same buffer with the concentration gradient from 0 M to 0.4 M sodium chloride. The active fraction thus obtained was concentrated using an ultrafiltration membrane (fraction molecular weight 10,000), applied to Superdex 200 HR 10/30 (manufactured by Amersham Pharmacia Biotech) for gel filtration by FPLC, and eluted with 50 mM Tris-hydrochloric acid buffer (pH 8.0) containing 0.15 M sodium chloride. The resulting active fraction was analyzed by SDS-polyacrylamide electrophoresis. As a result, D-amino acid oxidase was detected as a single band, confirming the purity of the purified enzyme.

Example 2

Properties of D-amino Acid Oxidase

The properties of the purified D-amino acid oxidase obtained in Example 1 were examined as follows.

[Specific Activity]

The activity of the D-amino acid oxidase was measured by quantifying hydrogen peroxide produced in the reaction by an enzyme method using peroxidase. Hydrogen peroxide was quantified by an enzyme method as follows. 250 µl of a chromogenic solution containing 50 mM DL-phenylalanine, 0.80 mM 4-aminoantipyrine, 1.31 mM N-ethyl-N-(2-hydroxy-3-sulfopropyl)-m-toluidine, 6 u/ml peroxidase (manufactured by TOYOBO Inc.) and 50 mM Tris-hydrochloric acid buffer (pH 8.0) was mixed with 50 µl of an appropriately diluted enzyme solution, and the mixture was reacted at 30° C. for 30 min. Absorption at 555 nm was measured, and the amount of hydrogen peroxide produced in the reaction mixture was quantified based on the analytical curve prepared in advance. The amount of the enzyme that produced 1 µmol of hydrogen peroxide in 1 minute was defined as 1 unit. In addition, protein was quantified according to a Bradford method using BSA as a standard protein. The specific activity of the purified D-amino acid oxidase was 44.8 units/mg protein (30° C.).

Moreover, the D-amino acid oxidase activity for examining the properties of the enzyme shown below was measured as follows. 250 µl of a substrate solution containing 100 mM DL-phenylalanine and 50 mM Tris-hydrochloric acid buffer (pH 8.0) was maintained at 30° C. (each temperature for determining the range of operative temperature and the optimal temperature) for 5 min, mixed with 50 µl of an appropriately diluted enzyme solution, and the mixture was reacted at 30° C. (each temperature for determining the range of operative temperature and the optimal temperature) for 5 min. 10 µl of 3N HCl was added to stop the reaction. Then, 500 µl of a chromogenic solution containing 0.80 mM 4-aminoantipyrine, 1.31 mM N-ethyl-N-(2-hydroxy-3-sulfopropyl)-m-toluidine, 6 u/ml peroxidase (manufactured by TOYOBO Inc.) and 50 mM Tris-hydrochloric acid buffer (pH 8.0), which was maintained at 30° C. for 5 min, was mixed with 100 µl of the aforementioned reaction mixture. Absorption at 555 nm was measured, and the amount of hydrogen peroxide produced in the reaction mixture was quantified based on the analytical curve prepared in advance.

[Measurement of Km Value]

Figure 2:
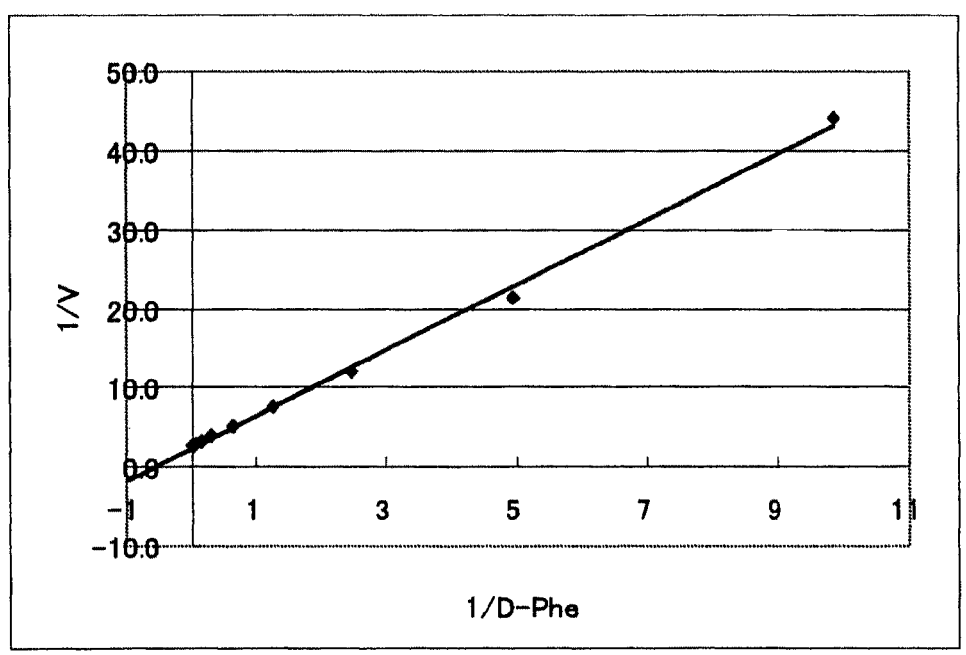
FIG. 2 is a graph showing a Km value relative to D-Phe of D-amino acid oxidase as an embodiment of the present invention.

Using D-Phe as a substrate, the activity was measured at various substrate concentrations and the Km value relative to D-Phe was determined. From the results shown in FIG. 2, the Km value relative to D-Phe was about 1.7 (not less than 1.6 and not more than 1.8) mM. In FIG. 2, the horizontal axis shows the reciprocal plot of the substrate concentration and the vertical axis shows the reciprocal plot of the activity.

[Range of Reaction Temperature and Optimal Temperature]

Figure 3:
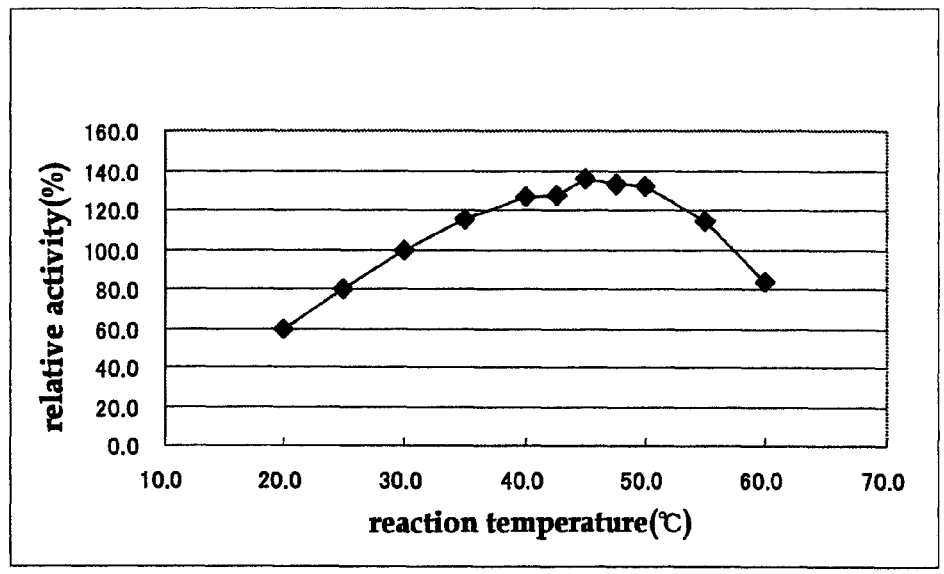
FIG. 3 is a graph showing the relationship (including optimal temperature) between the operative temperature and relative activity of D-amino acid oxidase as an embodiment of the present invention.

The range of reaction temperature and the optimal temperature were examined. FIG. 3 shows the relative activities at various temperatures when the activity at 30° C. is 100%. The enzyme was highly active at least within the examined range of 20-60° C., and the optimal temperature was 40° C.-50° C.

[Range of Reaction pH and Optimal pH]

Figure 4:
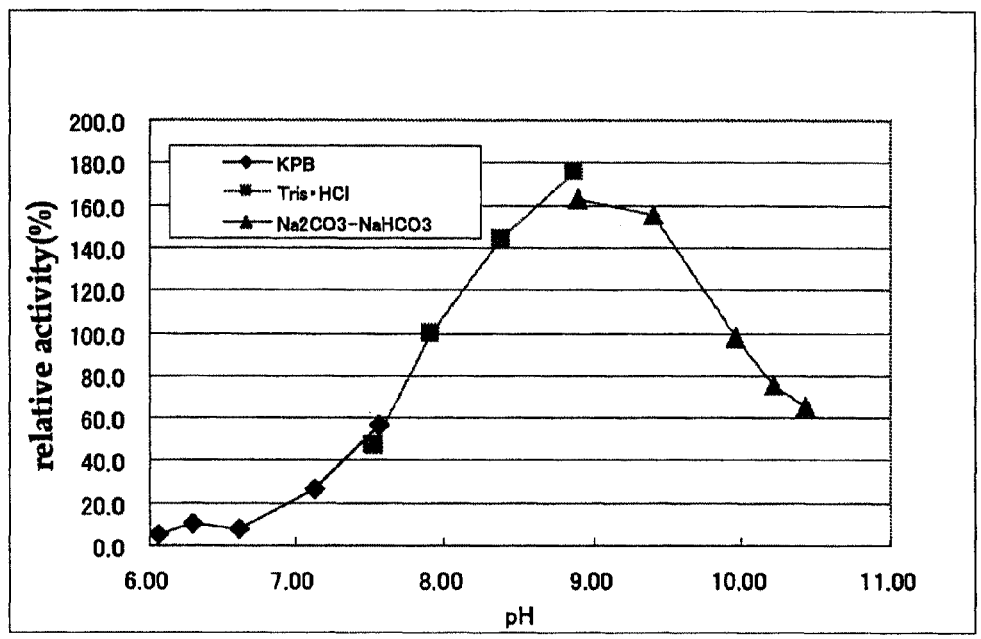
FIG. 4 is a graph showing the relationship (including optimal pH) between the operative pH and relative activity of D-amino acid oxidase as an embodiment of the present invention.

The range of reaction pH and the optimal pH were examined. FIG. 4 shows relative activity at each pH value examined using a potassium phosphate buffer for the pH range of 6.0 to 7.5, a Tris-hydrochloric acid buffer for the pH range of 7.5 to 8.8, and a sodium carbonate buffer for the pH range of 8.8 to 10.5, with the activity at pH 8.0 as 100%. The enzyme was active at least within the examined range of pH 6-10.5, and the optimal pH was 8.5-9.5.

[Temperature Stability]

Figure 5:
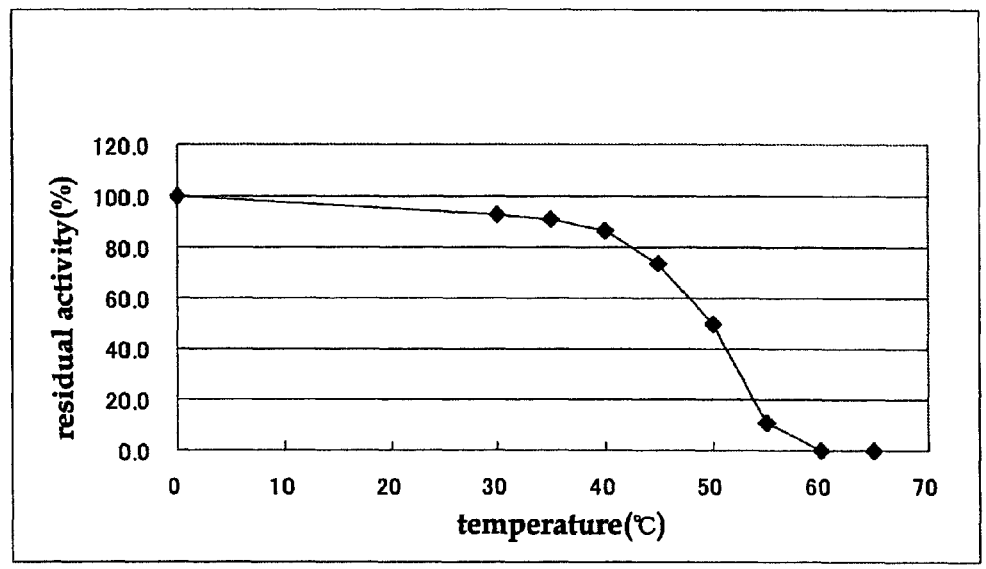
FIG. 5 is a graph showing the relationship (including temperature stability) between the treated temperature and residual activity of D-amino acid oxidase as an embodiment of the present invention.

The temperature stability of the enzyme was measured based on the residual activity after a treatment at each temperature for 10 min. As shown in FIG. 5, the enzyme was stable at 40° C. or lower.

[pH Stability]

Figure 6:
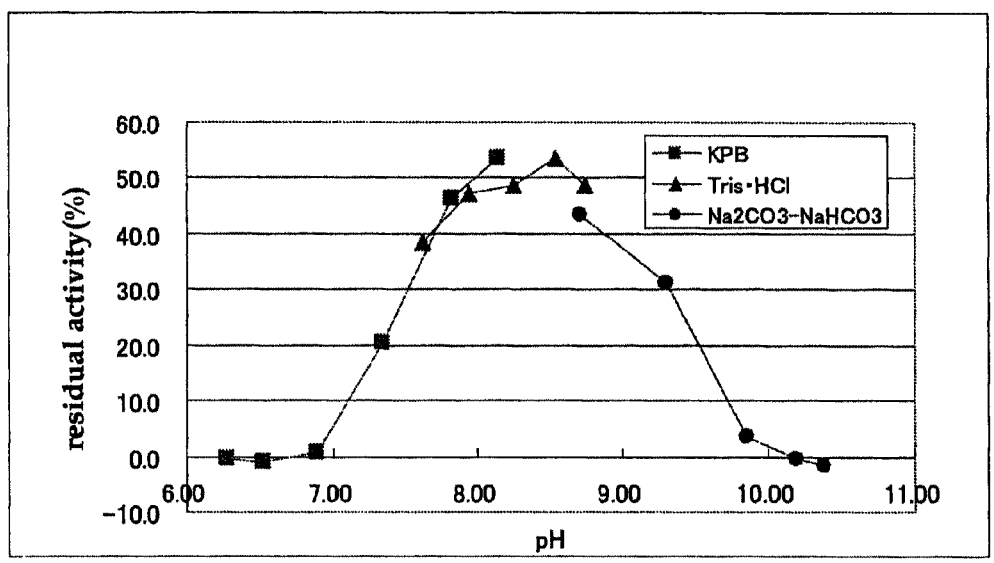
FIG. 6 is a graph showing the relationship (including pH stability) between the treated pH and residual activity of D-amino acid oxidase as an embodiment of the present invention.

The pH stability was examined. FIG. 6 shows the residual activity of the enzyme after a treatment at 30° C. for 16 hr at each pH with the activity at pH 8.0 as 100%. A potassium phosphate buffer was used for the pH range of 6.2 to 8.1, a Tris-hydrochloric acid buffer was used for the pH range of 7.6 to 8.7, and a sodium carbonate buffer was used for the pH range of 8.7 to 10.4. This enzyme was comparatively stable at pH 7.8-8.7.

[Measurement of Molecular Weight]

The molecular weight was measured in comparison with the elution time of the standard protein by gel filtration chromatography and found to be about 252,000 (not less than 230,000 and not more than 280,000). The subunit molecular weight was measured in comparison with the mobility of the standard protein by SDS-polyacrylamide electrophoresis and found to be about 42,000 (not less than 39,000 and not more than 45,000). The D-amino acid oxidase of the present invention had a hexameric structure consisting of identical subunits.

[Substrate Specificity]

The substrate specificity of the purified D-amino acid oxidase was examined. The substrate DL-phenylalanine used in the aforementioned enzyme activity assay was changed to each substrate, and the enzyme activity was measured. Table 1 shows the relative activity values with the activity to D-Phe as 100%.

TABLE 1

Relative activity values

| substrate | relative activity (%) |
| --- | --- |
| D-Phe | 100.0 |
| D-Ala | 129.1 |
| D-Leu | 96.7 |
| D-Met | 100.5 |
| D-Pro | 44.3 |
| D-Val | 27.3 |
| D-Ile | 16.6 |
| D-Ser | 11.3 |
| D-Asn | 5.8 |
| D-Gln | 5.8 |
| D-Thr | 4.7 |
| D-Arg | 0.05 |
| D-Asp | 0.0 |
| D-Glu | 0.0 |
| D-Lys | 0.0 |
| D-p-F-Phe | 167.2 |
| D-3,4-dihydroxy-phenylglycine | 5.7 |
| D-His | 4.2 |
| DL-α-phenylbutyric acid | 194.7 |
| DL-Norvaline | 93.8 |
| DL-2-amino-4-Br-butyric acid | 17.2 |

TABLE 1-continued

Relative activity values

| substrate | relative activity (%) |
| --- | --- |
| β-Cl-DL-Ala | 17.6 |
| L-Phe | 0.0 |
| L-Ala | 0.0 |
| L-Leu | 0.0 |
| L-Met | 0.0 |
| L-Pro | 0.0 |
| L-Norvaline | 0.0 |
| Gly | 0.0 |

Example 3

Determination of Internal Amino Acid Sequence of D-amino Acid Oxidase

The D-amino acid oxidase purified in Example 1 was reacted with lysylendopeptidase in the presence of 4 M urea. The resulting polypeptide fragment was purified by reversed-phase HPLC, and the internal amino acid sequence of the D-amino acid oxidase was determined using a vapor phase protein sequencer.

Example 4

Isolation of D-amino Acid Oxidase Gene

A chromosomal DNA was prepared using an UltraClean Microbial DNA Isolation Kit (manufactured by MO BIO Laboratories, Inc.) from microbial cells obtained by culturing Candida intermedia NBRC0761 strain in the same manner as in Example 1.

Thereafter, PCR was performed using DNA primers (Primer-1: Sequence Listing SEQ ID NO: 3, and Primer-2: Sequence Listing SEQ ID NO: 4) designed based on a site homologous to the known D-amino acid oxidase sequence with the chromosomal DNA obtained above as a template. PCR was performed by adding 0.25 µl of Ex taq DNA polymerase (manufactured by Takara Bio Inc.), 5 µl of 10×Ex taq buffer (manufactured by Takara Bio Inc.), 4 µl of each 2.5 mM dNTP solution, and 1 µl each of aqueous primer solutions (20 µM) to 100 ng of template DNA, and then sterilized water to give a reaction mixture in a total amount of 50 µl; subjecting the mixture to 30 cycles of heat denaturation (94° C., 60 sec), annealing (40° C., 60 sec) and elongation reaction (7220 C., 60 sec); and cooling the mixture to 4° C.

As a result, about 750 bp DNA fragment of a part of the desired D-amino acid oxidase gene (referred to as a partial gene) was obtained.

Thereafter, the following operation was performed to obtain the full length of the desired gene. In the above-mentioned partial gene, DNA primers (Primer-3: Sequence Listing SEQ ID NO: 5, and Primer-4: Sequence Listing SEQ ID NO: 6) toward the outside direction of the partial gene were synthesized based on the base sequences corresponding to both N-terminal side and C-terminal side of the enzyme. Inverse PCR was performed using these primers and, as a template, a DNA obtained by digesting the chromosomal DNA obtained earlier with a restriction enzyme HincII and cyclizing with a T4 DNA ligase. PCR was performed under the same conditions as above except that the annealing temperature was set to 57° C.

As a result, an about 1.5 kbp DNA fragment containing the gene outside the partial gene already obtained was amplified. After determining the base sequence of this DNA fragment, the base sequence was combined with the base sequence of the above partial gene to determine the full base sequence of the D-amino acid oxidase gene including the sequence from the initiation codon to the stop codon shown in Sequence Listing SEQ ID NO: 7. As a result of the analysis of the base sequence, the D-amino acid oxidase gene obtained from the chromosomal DNA contained 2 exons and 1 intron.

The following operation was performed to afford a intronless D-amino acid oxidase gene. First, from the microbial cells obtained by culturing *Candida intermedia* NBRC0761 strain in the same manner as in Example 1, the total RNA was prepared using ISOGEN (manufactured by Nippon Gene Co., Ltd.) and by using the RNA as template, a complementary strand DNA (cDNA) was prepared using TaKaRa RNA LA PCR Kit (AMV) Ver. 1.1 (manufactured by TaKaRa). Using primers (Primer-5: Sequence Listing SEQ ID NO: 8, and Primer-6: Sequence Listing SEQ ID NO: 9) having a sequence in which the N-terminal part and C-terminal part of the D-amino acid oxidase gene were linked with the cleavage site of restriction enzymes NdeI and SacI, respectively, the DNA therebetween was amplified by PCR using cDNA as a template, whereby a DNA fragment having the open reading frame shown in Sequence Listing SEQ ID NO: 2 intronless was obtained.

PCR was carried out under the same conditions as in Example 11-1 below except that the amount of cDNA used as a template was 50 ng and the annealing temperature was set to 6020 C.

It was confirmed that the deduced amino acid sequence to be encoded by the obtained DNA fragment contained the internal amino acid sequence of the D-amino acid oxidase determined in Example 3 and that the obtained DNA fragment was a gene coding for the purified enzyme of Example 1.

Example 5

Preparation of Recombinant Plasmid Expressing D-amino Acid Oxidase Gene

The DNA fragment obtained in Example 4 was digested with the restriction enzymes NdeI and SacI. By ligating, using a T4 DNA ligase, the DNA fragment with the vector plasmid pUCNT (which can be produced by those of ordinary skill in the art based on the description in the specification of WO94/03613) digested with the same enzymes, pCDA003 was obtained that is shown in the restriction enzyme map in FIG. 1 and designed to be able to express the D-amino acid oxidase gene in large amounts.

Example 6

Preparation of Transformant Using Recombinant DNA Containing D-amino Acid Oxidase Gene By mixing the plasmid pCDA003 obtained in Example 5 with the competent cells of *Escherichia coli* HB101 or JM109, the competent cells were transformed and plated on a medium (10 g of tryptone, 5 g of yeast extract, 10 g of sodium chloride, 15 g of agar, 100 mg of ampicillin, messed up to 1 l with deionized water, pH 7.0 before sterilization, ampicillin was added after sterilization), whereby a transformant *Escherichia coli* HB101 (pCDA003) (FERM BP-10639) or JM109 (pCDA003) (FERM BP-10638) containing a recombinant DNA containing the D-amino acid oxidase gene was obtained as a colony.

The obtained transformant colony was inoculated into 6 ml of a sterilized medium (16 g of tryptone, 10 g of yeast extract, 5 g of sodium chloride, 100 mg of ampicillin, messed up to 1 l with deionized water, pH 7.0 before sterilization, ampicillin was added after sterilization) in test tube, and aerobically cultured with shaking at 37° C. for 23 to 29 hr. Microbial cells were harvested by centrifugation from the obtained culture medium, suspended in 0.1 M Tris-hydrochloric acid buffer (pH 8.0), and disrupted by sonication. Thereafter, insoluble matter derived from the microbial cells was removed by centrifugation to give D-amino acid oxidase enzyme solution from the transformant. The activity of the D-amino acid oxidase was measured according to the method described in Example 2 using 0.05 ml of the obtained enzyme solution. As a result, the D-amino acid oxidase activity was confirmed.

Moreover, the transformant *Escherichia coli* HB101 (pCDA003) as obtained above was inoculated into 6 ml of a sterilized medium (16 g of tryptone, 10 g of yeast extract, 5 g of sodium chloride, 100 mg of ampicillin, messed up to 1 l with deionized water, pH 7.0 before sterilization, ampicillin was added after sterilization) in test tube, and then aerobically cultured with shaking at 37° C. for 24 hr. Microbial cells were harvested from the obtained culture medium by centrifugation, and the plasmid pCDA003 was recovered using a QIAprep Spin Miniprep Kit (manufactured by QIAGEN).

The transformant *Escherichia coli* HB101 (pCDA003) was deposited on Jul. 10, 2006, under receipt number FERM BP-10639 (a strain domestically deposited with the original deposition date of Jul. 19, 2005, and transferred to an international deposition under the Budapest Treaty) and the transformant *Escherichia coli* JM109 (pCDA003) was deposited on Jul. 10, 2006, under receipt number FERM BP-10638 (a strain domestically deposited with the original deposition date of Jun. 28, 2005, and transferred to an international deposition under the Budapest Treaty) at the National Institute of Advanced Industrial Science and Technology, the International Patent Organism Depositary (1-1 Tsukuba-shi Higashi 1-chome, Ibaragi-ken, 305-8566).

Example 7

Synthesis of L-amino Acid or 2-Oxo Acid by Resolution Reaction Using Purified D-amino Acid Oxidase A reaction was carried out at 30° C. for 13 hr using 25 μg of the D-amino acid oxidase purified in Example 1, mg of DL-phenylalanine, 2 μl of catalase (Catazyme 25L, manufactured by Novozyme) and 1 ml of a 50 mM Tris-hydrochloric acid buffer (pH 8.0). Thereafter, the reaction mixture was then diluted 50 fold with an aqueous $HClO_4$ solution (pH 1.5). The centrifugation supernatant was analyzed by HPLC to quantify amino acid. The HPLC analysis was carried out under the following conditions. column: CROWNPAK CR+ (4.6 mm×150 mm, manufactured by Daicel), eluent: aqueous $HClO_4$ solution (pH 1.5), flow rate: 0.9 ml/min, column temperature: 30° C., detection: 210 nm. As a result, L-phenylalanine having an optical purity of 100% ee was obtained in a reaction yield of 47.5 mol %. Furthermore, the reaction mixture was diluted 100 fold with 10 mM potassium phosphate buffer (pH 2.0)/acetonitrile=3/1, and the centrifugation supernatant was analyzed by HPLC to quantify 2-oxo acid.

The HPLC analysis was carried out under the following conditions. column: COSMOSIL 5C18ARII (4.6 mm×250 mm, manufactured by Nacalai Tesque), eluent: 10 mM potassium phosphate buffer (pH 2.0)/acetonitrile=5/1, flow rate: 1.0 ml/min, column temperature: 30° C., detection: 210 nm. As a result, phenylpyruvic acid was produced in a reaction yield of 44.4 mol %.

Example 8

Synthesis of L-amino Acid by Resolution Reaction Using Strain Having D-Amino Acid Oxidase Activity Microbial cells in an amount corresponding to that found in 4 ml of a culture medium containing *Candida intermedia* NBRC0761 strain cultured in the same manner as in Example 1 was harvested by centrifugation and suspended in 2 ml of a 50 mM Tris-hydrochloric acid buffer (pH 8.0). The cells were physically disrupted by glass beads and then subjected to centrifugation, and the supernatant was recovered as a crude enzyme solution. A reaction was carried out at 30° C. for 16 hr using 125 μl of the obtained crude enzyme solution, 1.25 mg of DL-phenylalanine, 0.05 μl of catalase (Catazyme 25L, manufactured by Novozyme) and 125 μl of a 50 mM Tris-hydrochloric acid buffer (pH 8.0). The reaction mixture was then diluted 50 fold with an aqueous $HClO_4$ solution (pH 1.5), and the centrifugation supernatant was analyzed by HPLC. % The HPLC analysis was carried out under the conditions described in Example 7. As a result, L-phenylalanine having an optical purity of 93.7% ee was obtained in a reaction yield of 54.5 mol %.

Example 9

Synthesis of L-amino Acid or 2-oxo Acid by Resolution Reaction Using Transformant The transformant *Escherichia coli* HB101 (pCDA003) (FERM BP-10639) or JM109 (pCDA003) (FERM BP-10638) having a D-amino acid oxidase activity obtained in Example 6 was harvested from a culture medium from centrifugation and suspended in 0.1 M Tris-hydrochloric acid buffer (pH 8.0). The obtained microbial cells were disrupted by sonication and subjected to centrifugation, and the supernatant was recovered as a crude enzyme solution. Each crude enzyme solution was reacted with each of DL-phenylalanine, DL-4-fluoro-phenylalanine, DL-Norvaline and β-chloro-DL-alanine to synthesize the corresponding L-amino acid or 2-oxo acid. Examples of each synthesis reaction are given below.

(9-1) Synthesis of L-phenylalanine and Phenylpyruvic Acid from DL-phenylalanine

Microbial cells in an amount corresponding to that found in 10 ml of the culture medium containing the transformant *Escherichia coli* HB101 (pCDA003) (FERM BP-10639) having a D-amino acid oxidase activity described above was harvested by centrifugation and suspended in 1 ml of 0.1 M Tris-hydrochloric acid buffer (pH 8.0). The obtained cells were disrupted by sonication and subjected to centrifugation. The supernatant was recovered as a crude enzyme solution. A reaction was carried out at 30° C. for 18 hr using 100 μl of the obtained crude enzyme solution, 10 mg of DL-phenylalanine, 2 μl of catalase (Catazyme 25L, manufactured by Novozyme) and 0.95 ml of 0.1 M Tris-hydrochloric acid buffer (pH 8.0). The reaction mixture was then diluted 50 fold with an aqueous $HClO_4$ solution (pH 1.5), and the centrifugation supernatant was analyzed by HPLC to quantify amino acid.

The HPLC analysis was carried out under the same conditions as in Example 7. As a result, L-phenylalanine having an optical purity of 100% ee was obtained in a reaction yield of 50.8 mol %. Furthermore, the reaction mixture was diluted 100 fold with 10 mM potassium phosphate buffer (pH 2.0)/acetonitrile=3/1, and the centrifugation supernatant was analyzed by HPLC to quantify 2-oxo acid. The HPLC analysis was carried out under the same conditions as in Example 7. As a result, phenylpyruvic acid was produced in a reaction yield of 41.9 mol %.

(9-2) Synthesis of L-phenylalanine and Phenylpyruvic Acid from DL-phenylalanine

Microbial cells in an amount corresponding to that found in 10 ml of the culture medium containing the transformant *Escherichia coli* JM109 (pCDA003) (FERM BP-10638) having a D-amino acid oxidase activity described above was harvested by centrifugation and suspended in 1 ml of 0.1 M Tris-hydrochloric acid buffer (pH 8.0). The obtained cells were disrupted by ultrasonication and subjected to centrifugation. The supernatant was recovered as a crude enzyme solution. A reaction was carried out at 30° C. for 19 hr using 50 μl of the obtained crude enzyme solution, 10 mg of DL-phenylalanine, 2 μl of catalase (Catazyme 25L, manufactured by Novozyme) and 0.95 ml of 0.1 M Tris-hydrochloric acid buffer (pH 8.0). The reaction mixture was then diluted 50 fold with an aqueous $HClO_4$ solution (pH 1.5), and the centrifugation supernatant was analyzed by HPLC to quantify amino acid.

The HPLC analysis was carried out under the same conditions as in Example 7. As a result, L-phenylalanine with an optical purity of 100% ee was obtained in a reaction yield of 49 mol %. Furthermore, the reaction mixture was diluted 100 fold with 10 mM potassium phosphate buffer (pH 2.0)/acetonitrile=3/1, and the centrifugation supernatant was analyzed by HPLC to quantify 2-oxo acid. The HPLC analysis was carried out under the same conditions as in Example 7. As a result, phenylpyruvic acid was prepared in a reaction yield of 48 mol %.

(9-3) Synthesis of L-4-fluoro-phenylalanine from DL-4-fluoro-phenylalanine

A reaction was carried out at 30° C. for 19 hr using 50 μl of a crude enzyme solution prepared in the same manner as in Example (9-2) from microbial cells in an amount corresponding to that found in 10 ml of the culture medium containing the transformant *Escherichia coli* JM109 (pCDA003) (FERM BP-10638) having a D-amino acid oxidase activity described above, 10 mg of DL-4-fluoro-phenylalanine, 2 μl of catalase (Catazyme 25L, manufactured by Novozyme) and 0.95 ml of 0.1 M Tris-hydrochloric acid buffer (pH 8.0). The reaction mixture was then diluted 100 fold with an aqueous $HClO_4$ solution (pH 1.5), and the centrifugation supernatant was analyzed by HPLC.

The HPLC analysis was carried out under the following conditions. column: CROWNPAK CR+ (4.6 mm×150 mm, manufactured by Daicel), eluent: aqueous $HClO_4$ solution (pH 1.5), flow rate: 0.5 ml/min, column temperature: 30° C., detection: 210 nm. As a result, L-4-fluoro-phenylalanine having an optical purity of 100% ee was obtained in a reaction yield of 51 mol %.

(9-4) Synthesis of L-Norvaline and 2-oxovaleric Acid from DL-Norvaline

A reaction was carried out at 30° C. for 1 hr using 50 μl of a crude enzyme solution prepared in the same manner as in Example (9-2) from microbial cells in an amount corresponding to that found in 10 ml of the culture medium containing the transformant *Escherichia coli* JM109 (pCDA003) (FERM BP-10638) having a D-amino acid oxidase activity described above, 10 mg of DL-Norvaline, 2 µl of catalase (Catazyme 25L, manufactured by Novozyme) and 0.95 ml of 0.1 M Tris-hydrochloric acid buffer (pH 8.0). The reaction mixture was then diluted 10 fold with an aqueous 2 mM $CuSO_4$ solution/methanol=19/1, and the centrifugation supernatant was analyzed by HPLC to quantify amino acid.

The HPLC analysis was carried out under the following conditions. columns: Develosil ODS-HG3 (4.6 mm×150 mm, manufactured by NOMURA CHEMICAL CO., LTD.)+SUMICHIRAL OA-5000 (4.6 mm×150 mm, manufactured by Sumika Chemical Analysis Service, Ltd.), eluent: 2 mM aqueous $CuSO_4$ solution/methanol=19/1, flow rate: 0.7 ml/min, column temperature: 30° C., detection: 254 nm. As a result, L-Norvaline having an optical purity of 100% ee was obtained in a reaction yield of 50.3 mol %. Furthermore, the reaction mixture was diluted 10 fold with 10 mM potassium phosphate buffer (pH 2.0)/acetonitrile=3/1, and the centrifugation supernatant was analyzed by HPLC to quantify 2-oxo acid. The HPLC analysis was carried out under the following conditions. column: COSMOSIL 5C18ARII (4.6 mm×250 mm, manufactured by Nacalai Tesque), eluent: 10 mM potassium phosphate buffer (pH 2.0)/acetonitrile=19/1, flow rate: 1.0 ml/min, column temperature: 30° C., detection: 210 nm. As a result, 2-oxo-valeric acid was produced in a conversion rate of 58.8 mol %.

(9-5) Synthesis of β-chloro-L-alanine from β-chloro-DL-alanine

A reaction was carried out at 30° C. for 1 hr using 50 µl of a crude enzyme solution prepared in the same manner as in Example (9-2) from microbial cells in an amount corresponding to that found in 10 ml of the culture medium containing the transformant *Escherichia coli* JM109 (pCDA003) (FERM BP-10638) having a D-amino acid oxidase activity described above, 5 mg of β-chloro-DL-alanine, 2 µl of catalase (Catazyme 25L, manufactured by Novozyme) and 0.95 ml of 0.1 M Tris-hydrochloric acid buffer (pH 8.0). The reaction mixture was then diluted 5 fold with 2 mM aqueous $CuSO_4$ solution/methanol=19/1, and the centrifugation supernatant was analyzed by HPLC to quantify amino acid. The amino acid quantification by HPLC analysis was carried out under the same conditions as in Example (9-4). As a result, β-chloro-L-alanine having an optical purity of 99.2% ee was obtained in a reaction yield of 47.1 mol %.

Example 10

Synthesis of L-amino Acid Using Transformant

The transformant *Escherichia coli* HB101 (pCDA003) (FERM BP-10639) and JM109 (pCDA003) (FERM BP-10638) having a D-amino acid oxidase activity obtained in Example 6 were harvested from each culture medium by centrifugation, and each cell was suspended in 0.1 M Tris-hydrochloric acid buffer (pH 8.0). The obtained microbial cells were disrupted by ultrasonication and then subjected to centrifugation to recover the supernatant as a crude enzyme solution. Furthermore, a transformant having a formate dehydrogenase activity obtained according to the method described below was harvested from a culture medium by centrifugation and suspended in 0.1 M Tris-hydrochloric acid buffer (pH 8.0). The obtained microbial cells were disrupted by ultrasonication and then subjected to centrifugation to recover the supernatant as a crude enzyme solution. Moreover, a transformant having a phenylalanine dehydrogenase activity and a transformant having a leucine dehydrogenase activity, both of which were produced according to the method described below, were harvested from each culture medium by centrifugation and each transformant was suspended in 0.1 M Tris-hydrochloric acid buffer (pH 8.0). The microbial cells were disrupted by sonication and subjected to centrifugation, and the supernatants were recovered as crude enzyme solutions. Each crude enzyme solution was reacted with each of DL-phenylalanine, DL-4-fluoro-phenylalanine, DL-Norvaline and DL-leucine, and the corresponding L-amino acids were synthesized by a stereo inversion reaction.

The culture medium of a transformant having a formate dehydrogenase activity was obtained as follows. *Escherichia coli* HB101 (pFT002) (FERM BP-7673), which is a transformant having a formate dehydrogenase activity, was inoculated into a 10 ml of a sterilized medium (16 g of tryptone, 10 g of yeast extract, 5 g of sodium chloride, 1 l of water, pH 7 before sterilization) in test tube and cultured while shaking at 30° C. for 24 hr. Furthermore, a culture medium containing a transformant having a phenylalanine dehydrogenase activity prepared according to the method described in Reference Example 1 below and a culture medium containing a transformant having a leucine dehydrogenase activity prepared according to the method described in Reference Example 2 below were both obtained as follows. A transformant having a phenylalanine dehydrogenase activity or a transformant having a leucine dehydrogenase activity was inoculated into a 10 ml of a sterilized medium (16 g of tryptone, 10 g of yeast extract, 5 g of sodium chloride, 1 l of water, pH 7 before sterilization) in test tube and cultured while shaking at 30° C. for 24 hr.

(10-1) Synthesis of L-phenylalanine from DL-phenylalanine

Microbial cells in an amount corresponding to that found in 10 ml of the culture medium of the transformant *Escherichia coli* HB101 (pCDA003) (FERM BP-10639) having a D-amino acid oxidase activity described above, microbial cells in an amount corresponding to that found in 10 ml of the culture medium of the transformant having a phenylalanine dehydrogenase activity described above, and microbial cells in an amount corresponding to that found in 10 ml of the culture medium of the transformant having a formate dehydrogenase activity described above were each harvested by centrifugation and suspended in a 1 ml of 0.1 M Tris-hydrochloric acid buffer (pH 8.0). The cells were disrupted by sonication and subjected to centrifugation. The supernatant was recovered as a crude enzyme solution. A reaction was carried out at 30° C. for 13 hr using 50 µl of each of the obtained crude enzyme solutions, 10 mg of DL-phenylalanine, 2 µl of catalase (Catazyme 25 L, manufactured by Novozyme), 0.18 mg of $NAD^+$, 7.0 mg of ammonium formate and 0.85 ml of 0.1 M Tris-hydrochloric acid buffer (pH 8.0). The reaction mixture was then diluted 50 fold with an aqueous $HClO_4$ solution (pH 1.5), and the centrifugation supernatant was analyzed by HPLC to quantify amino acid. The amino acid quantification by HPLC analysis was carried out under the same conditions as in Example 7. As a result, L-phenylalanine having an optical purity of 100% ee was obtained in a reaction yield of 95.6 mol % relative to the racemic amino acid.

(10-2) Synthesis of L-phenylalanine from DL-phenylalanine

Microbial cells in an amount corresponding to that found in 10 ml of the culture medium of the transformant *Escherichia coli* JM109 (pCDA003) (FERM BP-10638) having a D-amino acid oxidase activity described above, microbial cells in an amount corresponding to that found in 10 ml of the culture medium of the transformant having a phenylalanine dehydrogenase activity described above, and microbial cells in an amount corresponding to that found in 10 ml of the culture medium of the transformant having a formate dehydrogenase activity described above were each harvested by centrifugation and suspended in a 1 ml of 0.1 M Tris-hydrochloric acid buffer (pH 8.0). The cells were disrupted by sonication and subjected to centrifugation. The supernatant was recovered as a crude enzyme solution. A reaction was carried out at 30° C. for 19 hr using 50 μl of each of the obtained crude enzyme solutions, 10 mg of DL-phenylalanine, 2 μl of catalase (Catazyme 25L, manufactured by Novozyme), 0.18 mg of NAD$^+$, 7.0 mg of ammonium formate and 0.85 ml of 0.1 M Tris-hydrochloric acid buffer (pH 8.0). The reaction mixture was then diluted 100 fold with an aqueous HClO$_4$ solution (pH 1.5), and the centrifugation supernatant was analyzed by HPLC to quantify amino acid. The amino acid quantification by HPLC analysis was carried out under the same conditions as in Example 7. As a result, L-phenylalanine having an optical purity of 100% ee was obtained in a reaction yield of 95 mol % relative to the racemic amino acid.

(10-3) Synthesis of L-4-fluoro-phenylalanine from DL-4-fluoro-phenylalanine

A reaction was carried out at 30° C. for 19 hr using 50 μl of each of the crude enzyme solutions of transformants as prepared in Example (10-2) above, 10 mg of DL-4-phenylalanine, 2 μl of catalase (Catazyme 25L, manufactured by Novozyme), 0.18 mg of NAD$^+$, 7.0 mg of ammonium formate and 0.85 ml of 0.1 M Tris-hydrochloric acid buffer (pH 8.0). The reaction mixture was then diluted 100 fold with an aqueous HClO$_4$ solution (pH 1.5), and the centrifugation supernatant was analyzed by HPLC to quantify amino acid. The HPLC analysis was carried out under the same conditions as in Example (9-3). As a result, L-4-fluoro-phenylalanine having an optical purity of 100% ee was obtained in a reaction yield of 103 mol % relative to the racemic amino acid.

(10-4) Synthesis of L-Norvaline from DL-Norvaline

Microbial cells in an amount corresponding to that found in 10 ml of the culture medium of the transformant *Escherichia coli* JM109 (pCDA003) (FERM BP-10638) having a D-amino acid oxidase activity described above, microbial cells in an amount corresponding to that found in 10 ml of the culture medium of the transformant having a leucine dehydrogenase activity described above, and microbial cells in an amount corresponding to that found in 10 ml of the culture medium of the transformant having a formate dehydrogenase activity described above were each harvested by centrifugation and suspended in a 1 ml of 0.1 M Tris-hydrochloric acid buffer (pH 8.0). The cells were disrupted by sonication and subjected to centrifugation. The supernatant was recovered as a crude enzyme solution. A reaction was carried out at 30° C. for 3 hr using 100 μl of the obtained crude enzyme solution of *Escherichia coli* JM109 (pCDA003) (FERM BP-10638), 50 μl each of the transformant having a leucine dehydrogenase activity and the transformant having a formate dehydrogenase activity, 50 mg of DL-Norvaline, 10 μl of catalase (Catazyme 25L, manufactured by Novozyme), 0.89 mg of NAD$^+$, 16.1 mg of ammonium formate and 0.8 ml of 0.1 M Tris-hydrochloric acid buffer (pH 8.0). The reaction mixture was diluted 100 fold with 2 mM aqueous CuSO$_4$ solution/methanol=19/1, and the centrifugation supernatant was analyzed by HPLC to quantify amino acid. The HPLC analysis was carried out under the same conditions as in Example (9-4). As a result, L-Norvaline having an optical purity of 100% ee was obtained in a reaction yield of 95.6 mol % relative to the racemic amino acid.

(10-5) Synthesis of L-leucine from DL-leucine

A reaction was carried out at 30° C. for 6 hr using 30 μl of a crude enzyme solution of *Escherichia coli* JM109 (pCDA003) (FERM BP-10638), 25 μl of a crude enzyme solution of transformant having a leucine dehydrogenase activity and 100 μl of a crude enzyme solution of a transformant having a formate dehydrogenase activity, which were prepared in 10-4 above, in combination with 50 mg of DL-leucine, 10 μl of catalase (Catazyme 25L, manufactured by Novozyme), 0.89 mg of NAD$^+$, 16.1 mg of ammonium formate and 0.8 ml of 0.1 M Tris-hydrochloric acid buffer (pH 8.0). The reaction mixture was then diluted 50 fold with MilliQ water, and the reaction was stopped with 1N HCl. The centrifugation supernatant was analyzed by HPLC to quantify amino acid.

The HPLC analysis was carried out under the following conditions. column: SUMICHIRAL OA-5000 (4.6 mm×150 mm, manufactured by Sumika Chemical Analysis Service, Ltd.), eluent: 2 mM aqueous CuSO$_4$ solution/2-Propanol=19/1, flow rate: 0.9 ml/min, column temperature: 30° C., detection: 254 nm. As a result, L-leucine having an optical purity of 100% ee was obtained in a reaction yield of 103.1 mol % relative to the racemic amino acid.

Reference Example 1

Preparation of Transformant Having Phenylalanine Dehydrogenase Activity

*Bacillus badius* IAM11059 strain was inoculated into a sterilized medium (1.0% tryptone, 0.5% yeast extract and 0.5% sodium chloride, dissolved in deionized water, pH 7.0 before sterilization), and aerobically cultured with shaking at 30° C. for 48 hr. Microbial cells were collected from the obtained culture medium by centrifugation, and a chromosomal DNA was obtained from the resulting cultivated microbial cells by the Marmur method. A DNA primer (Primer-7: Sequence Listing SEQ ID NO: 10 and Primer-8: Sequence Listing SEQ ID NO:11) wherein restriction enzymes NdeI site and PstI site linked to the N-terminal part and the C-terminal part, respectively, was designed based on the base sequence of the phenylalanine dehydrogenase gene of *Bacillus badius* IAM11059 strain known from Bisci. Biotechnol. Biochem., 1995, Vol. 59, No. 10, page 1994, and PCR was performed using the aforementioned chromosomal DNA as a template. PCR was performed in the same manner as in Example 1-1 to be mentioned below except that the annealing temperature was set to 50° C. in the PCR conditions. The obtained DNA fragment was digested with restriction enzymes NdeI and PstI, and the DNA fragment and vector plasmid pUCNT (which can be produced by those of ordinary skill in the art based on the specification of W094/03613) digested with the same enzymes were ligated using a T4 DNA ligase to give a plasmid designed to express phenylalanine dehydrogenase in a large amount. By mixing the obtained plasmid with the competent cells of *Escherichia coli* HB101, the competent cells were transformed to prepare the transformant having a phenylalanine dehydrogenase activity.

Reference Example 2

Preparation of a Transformant Having a Leucine Dehydrogenase Activity

*Bacillus sphaericus* NBRC3341 strain was inoculated into a sterilized medium C (1.0% tryptone, 0.5% yeast extract and 0.5% sodium chloride, dissolved in deionized water, pH 7.0 before sterilization), and aerobically cultured with shaking at 30° C. for 48 hr. Using, as a template, the chromosomal DNA obtained by the Marmur method (see J. Mol. Biol., 3, 208 (1961)) from cultivated microbial cells obtained by collecting microbial cells from the obtained culture medium by centrifugation, and a DNA primer (Primer-9: Sequence Listing SEQ ID NO: 12 and Primer-10: Sequence Listing SEQ ID NO: 13), PCR was performed. PCR was performed in the same manner as in Example 11-1 to be mentioned below except that the annealing temperature was set to 50° C. in the PCR conditions. The DNA amplified fragment obtained by PCR was digested with restriction enzymes EcoRI and SacI, and the DNA fragment and vector plasmid pUCT (plasmid vector wherein NdeI site of pUCNT (which can be produced by those of ordinary skill in the art based on the description in the specification of WO94/03613) is destroyed) digested with the same enzymes were ligated using a T4 DNA ligase to give a plasmid designed to express leucine dehydrogenase.

By mixing the obtained plasmid with the competent cells of *Escherichia coli* HB101, the competent cells were transformed to prepare the transformant having a leucine dehydrogenase activity. The obtained transformant was inoculated into 6 ml of medium C sterilized in test tube, and aerobically cultured with shaking at 37° C. for 24 hr. Microbial cells were collected from the obtained culture medium by centrifugation, a plasmid was extracted using a QIAprep Spin Miniprep Kit (manufactured by QIAGEN) to recover a plasmid designed to express a leucine dehydrogenase.

Example 11

Preparation of Transformant Having D-amino Acid Oxidase Activity, Amino Acid Dehydrogenase Activity and Activity of an Enzyme Having Coenzyme-Regenerating Ability (11-1) Preparation of Transformant having D-amino acid oxidase, leucine dehydrogenase and formate dehydrogenase Activities PCR was performed using DNA primers (Primer-11: Sequence Listing SEQ ID NO: 14, and Primer-12: Sequence Listing SEQ ID NO: 15) and as a template, an expression plasmid pCDA003 obtained in Example 6 designed to express a D-amino acid oxidase derived from *Candida intermedia* NBRC0761 strain. PCR was performed by adding 0.25 µl of Pyrobest DNA polymerase (manufactured by Takara Bio Inc.), 5 µl of 10×Pyrobest Buffer II (manufactured by Takara Bio Inc.), 4 µl each of 2.5 mM dNTP solutions and 2 µl each of aqueous primer solutions (20 µM) to 100 ng of the template DNA, and then sterilized water to give a reaction mixture in a total amount of 50 µl; subjecting the mixture to 25 cycles of heat denaturation (96° C., 30 sec), annealing (60° C., 30 sec) and elongation reaction (72° C., 90 sec); and cooling the mixture to 4° C.

Figure 7:
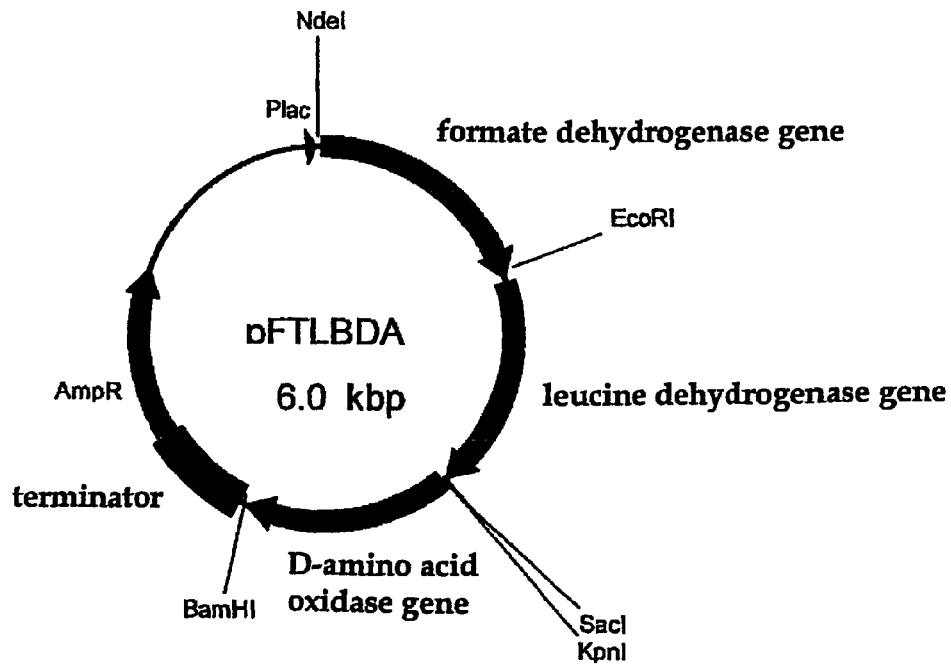
FIG. 7 shows the construction of recombinant plasmid pFTLBDA containing a D-amino acid oxidase gene, a leucine dehydrogenase gene, and a formate dehydrogenase gene as an embodiment of the present invention.

The DNA amplified fragment obtained by PCR was digested with the restriction enzymes KpnI and BamHI. By ligating the DNA fragment with a fragment prepared by digesting with these enzymes a plasmid pFTLB obtained in Reference Example 4 below, which is designed to express a leucine dehydrogenase and formate dehydrogenase, using a T4 DNA ligase, thereby giving a plasmid pFTLBDA shown in FIG. 7 that is designed to express a D-amino acid oxidase, leucine dehydrogenase and formate dehydrogenase.

By mixing the plasmid thus obtained with the competent cells of *Escherichia coli* HB101 (manufactured by Takara Bio Inc.), the competent cells were transformed to prepare the transformant *Escherichia coli* HB101 (pFTLBDA) having D-amino acid oxidase, leucine dehydrogenase and formate dehydrogenase activities.

(11-2) Preparation of Transformant Having D-amino Acid Oxidase, Leucine Dehydrogenase and Formate Dehydrogenase Activities By mixing both of a plasmid pFTLB designed to express a leucine dehydrogenase and formate dehydrogenase as obtained in Reference Example 4 below and a plasmid pSTNDA designed to express a D-amino acid oxidase as obtained in Reference Example 6 below with the competent cells of *Escherichia coli* HB101, the competent cells were transformed to prepare the transformant *Escherichia coli* HB101 (pFTLBDA, pSTNDA) having D-amino acid oxidase, leucine dehydrogenase and formate dehydrogenase activities.

Figure 8:
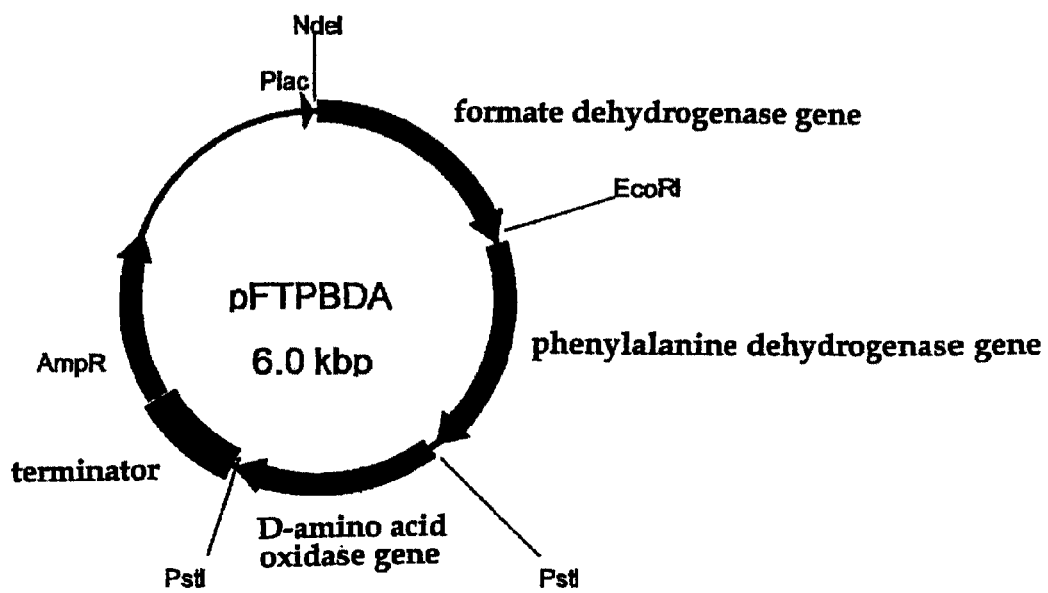
FIG. 8 shows the construction of recombinant plasmid pFTPBDA containing a D-amino acid oxidase gene, a phenylalanine dehydrogenase gene, and a formate dehydrogenase gene as an embodiment of the present invention.

(11-3) Preparation of Transformant having D-amino acid oxidase, phenylalanine dehydrogenase and formate dehydrogenase Activities PCR was performed with DNA primers (Primer-13: Sequence Listing SEQ ID NO: 16, and Primer-14: Sequence Listing SEQ ID NO: 17) using as a template an expression plasmid pCDA003 as obtained in Example 6 designed to express a D-amino acid oxidase derived from *Candida intermedia* NBRC0761 strain. PCR was performed in the same manner as in Example 11-1. The DNA amplified fragment obtained by PCR was digested with the restriction enzyme PstI. This DNA fragment was ligated, using a T4 DNA ligase, with a fragment prepared by digesting with the enzyme a plasmid pFTPB obtained in Reference Example 5 below and designed to express a phenylalanine dehydrogenase and formate dehydrogenase. By mixing the plasmid obtained by the ligase reaction with the competent cells of *Escherichia coli* HB101, the competent cells were transformed. Among the transformants, those that maintained a plasmid in which the D-amino acid oxidase gene was inserted in the same direction as the phenylalanine dehydrogenase gene and formate dehydrogenase gene were selected by sequencing the DNA sequence of the plasmid. As a result, a plasmid pFTPBDA as shown in FIG. 8 that is designed to express D-amino acid oxidase, phenylalanine dehydrogenase and formate dehydrogenase was obtained.

By mixing this plasmid pFTPBDA with the competent cells of *Escherichia coli* HB101, the competent cells were transformed once again to prepare the transformant *Escherichia coli* HB101 (pFTPBDA) having D-amino acid oxidase, phenylalanine dehydrogenase and formate dehydrogenase activities.

(11-4) Preparation of Transformant Having D-amino Acid Oxidase, Phenylalanine Dehydrogenase and Formate Dehydrogenase Activities By mixing both of a plasmid pFTPB designed to express phenylalanine dehydrogenase and formate dehydrogenase obtained in Reference Example 5 below and a plasmid pSTNDA designed to express a D-amino acid oxidase obtained in Reference Example 6 below with the competent cells of *Escherichia coli* HB101, the competent cells were transformed to prepare the transformant *Escherichia coli* HB101 (pFTPB, pSTNDA) having D-amino acid oxidase, phenylalanine dehydrogenase and formate dehydrogenase activities.

Example 12

Production of D-amino acid oxidase Using Transformant

The transformants each obtained in Example 11, Reference Example 6 below and Example 6 were inoculated into the sterile media shown in Table 2 and aerobically cultured with shaking at 30° C. for 24 hr.

Microbial cells were harvested from the obtained culture media by centrifugation, each suspended in 0.1 M Tris-hydrochloric acid buffer (pH 8.0) and disrupted by sonication. Insoluble matters derived from the microbial cells were removed by centrifugation, thereby giving D-amino acid oxidase enzyme solutions of these transformants. Using these enzyme solutions thus obtained, the D-amino acid oxidase activities were measured, and the results are shown in Table 2.

The results show that, compared with the transformant *Escherichia coli* HB101 (pCDA003) and *Escherichia coli* HB101 (pSTNDA), which have only the D-amino acid oxidase gene derived from the *Candida intermedia* NBRC0761 strain, the transformants *Escherichia coli* HB101 (pFTLBDA) and *Escherichia coli* HB101 (pFTLB, pSTNDA), which have the aforementioned D-amino acid oxidase gene, a leucine dehydrogenase gene and formate dehydrogenase gene, and transformants *Escherichia coli* HB101 (pFTPBDA) and *Escherichia coli* HB101 (pFTPB, pSTNDA), which have the aforementioned D-amino acid oxidase gene, a phenylalanine dehydrogenase gene and formate dehydrogenase gene, exhibited higher D-amino acid oxidase activities.

(Assay of D-amino Acid Oxidase Activity)

The assay of D-amino acid oxidase activities were carried out according to the method described in Example 2.

TABLE 2

| Run | Transformant | Medium (*1) | D-amino acid oxidase activity (%) (*2) |
|---|---|---|---|
| 1 | E. coli HB101 (pCDA003) | A | 100 |
| 2 | E. coli HB101 (pFTLBDA) | A | 1479 |
| 3 | E. coli HB101 (pFTPBDA) | A | 5225 |
| 4 | E. coli HB101 (pSTNDA) | B | 100 |
| 5 | E. coli HB101 (pFTLB, pSTNDA) | B | 138 |
| 6 | E. coli HB101 (pFTPB, pSTNDA) | B | 173 |

(*1) medium A: 1.6% Tryptone, 1.0% yeast extract, 0.5% sodium chloride and 0.01% ampicillin dissolved in deionized water, pH 7.0 before sterilization (ampicillin was added after sterilization)
medium B: 0.01% Chloramphenicol was added to medium A after sterilization
(*2) Values in Runs 1-3 are relative values when the D-amino acid oxidase activity of Run 1 is 100
Values in Runs 4-6 are relative values when the D-amino acid oxidase activity of Run 4 is 100

Example 13

Synthesis of L-Norvaline Using Transformant Having D-amino Acid Oxidase, Leucine Dehydrogenase and Formate Dehydrogenase Activities A transformant *Escherichia coli* HB101 (pFTLBDA) having D-amino acid oxidase, leucine dehydrogenase and formate dehydrogenase activities as obtained in Example 11-1 was inoculated into sterilized medium A (1.6% tryptone, 1.0% yeast extract, 0.5% sodium chloride, 0.01% ampicillin, dissolved in deionized water, pH 7.0 before sterilization, ampicillin was added after sterilization) and then aerobically cultured with shaking at 33° C. for 48 hr. Microbial cells were harvested by centrifugation from the culture medium thus obtained, and suspended in deionized water such that the concentration thereof would be 10-fold that in the culture medium. To 100 mg of racemic Norvaline were added the microbial cell suspension having 13 u of D-amino acid oxidase activity, 2 μl of catalase (Catazyme 25L, manufactured by Novozyme), 2 μl of Triton X-100, 0.59 mg of NAD and 43 mg of ammonium formate. Furthermore, the pH was adjusted to 8.0 with a 5M aqueous ammonia solution, and deionized water was added such that the reaction mixture thus prepared would have a volume of 2 ml. The reaction mixture was placed in a test tube and shaken at 30° C., and reacted for 8 hr while controlling the mixture at 8.0 with 2N sulfuric acid. The yield and optical purity of the produced L-Norvaline were analyzed by high performance liquid chromatography (HPLC). As a result, L-Norvaline having an optical purity of 100% ee was obtained in a reaction yield of 93.3% relative to the racemate.

The results showed that, in comparison with Comparative Example 1 given below in which a transformant having a D-amino acid oxidase activity and a transformant having leucine dehydrogenase and formate dehydrogenase activities are used, a high reactivity was exhibited without disrupting the microbial cells. (HPLC analysis conditions) column: SUMICHIRAL OA-5000 (4.6 mm×250 mm, manufactured by Sumika Chemical Analysis Service, Ltd.), mobile phase: 2 mM aqueous copper sulfate solution/methanol=95/5, flow rate: 1 ml/min, column temperature: 30° C., detection: 254 nm Example 14

Synthesis of L-tert-leucine Using Transformant Having D-amino Acid Oxidase, Leucine Dehydrogenase and Formate Dehydrogenase Activities Microbial cells were harvested by centrifugation from a culture medium containing a transformant *Escherichia coli* HB101 (pFTLBDA) cultured in the same manner as in Example 13 and suspended in deionized water such that the cell concentration would be 10-fold that in the culture medium to give a microbial cell suspension. A part of the suspension was sonicated to disrupt the microbial cells to give a crude enzyme solution.

To 50 mg of racemic tert-leucine were added the aforementioned microbial cell suspension having 20 u of D-amino acid oxidase activity, 5 μl of catalase (Catazyme 25L, manufactured by Novozyme), 0.79 mg of NAD and 19 mg of ammonium formate. Furthermore, the pH was adjusted to 8.0 with a 5M aqueous ammonia solution, and deionized water was added such that the reaction mixture thus prepared would have a volume of 1 ml. The reaction mixture was placed in a test tube and shaken at 30° C., and reacted for 42 hr while controlling the mixture at 8.0 with 2N sulfuric acid. The yield and optical purity of the produced L-tert-leucine were analyzed by a method similar to that in Example 3. As a result, L-tert-leucine having an optical purity of 100% ee was obtained in a reaction yield of 93.3% relative to the racemate.

In addition, when the above-mentioned crude enzyme solution was used instead of the microbial cell suspension in the same amount, L-tert-leucine having an optical purity of 83.2% ee was obtained in a reaction yield of 93.3% relative to the racemate. As can be understood from these results, the use of undisrupted microbial cells (microbial cell suspension) enhances reactivity compared with the use of a crude enzyme solution.

Comparative Example 1

Synthesis of L-Norvaline Using Transformant Having D-amino Acid Oxidase Activity and Transformant Having Leucine Dehydrogenase and Formate Dehydrogenase Activities A transformant *Escherichia coli* HB101 (pCDA003) (FERM BP-10639) having a D-amino acid oxidase activity, which was obtained in Example 6, was inoculated into sterilized medium A, and aerobically cultured with shaking at 37° C. for 30 hr. Microbial cells were harvested from the obtained culture medium by centrifugation, and suspended in deionized water such that the concentration of the microbial cells would be 10-fold that in the culture medium. A part of the suspension was sonicated to disrupt the microbial cells to give a crude enzyme solution containing D-amino acid oxidase. In addition, a transformant *Escherichia coli* HB101 (pFTLB) having a leucine dehydrogenase activity and a formate dehydrogenase activity, which was prepared by the method shown in Reference Example 4 to be mentioned below, was inoculated into sterilized medium A, and aerobically cultured with shaking at 33° C. for 48 hr. Microbial cells were harvested from the obtained culture medium by centrifugation, and suspended in deionized water such that the concentration of the microbial cells would be 10-fold that in the culture medium. A part of the suspension was sonicated to disrupt the microbial cells to give a crude enzyme solution containing a leucine dehydrogenase and a formate dehydrogenase.

To 50 mg of racemic Norvaline were added the microbial cell suspension of the aforementioned *Escherichia coli* HB101 (pCDA003) in the same amount as in Example 13, the aforementioned *Escherichia coli* HB101 (pFTLB) in the same amount as in Example 13, 1 µl of catalase (Catazyme 25 L, manufactured by Novozyme), 0.30 mg of NAD and 16 mg of ammonium formate. Furthermore, the pH was adjusted to 8.0 with a 5M aqueous ammonia solution, and deionized water was added such that the reaction mixture thus prepared would have a volume of 1 ml. The reaction mixture was placed in a test tube and shaken at 30° C., and reacted for 9 hr while controlling the mixture at 8.0 with 2N sulfuric acid. The yield and optical purity of the produced L-Norvaline were analyzed by a method similar to that in Example 3. As a result, L-Norvaline having an optical purity of 47.9% ee was obtained in a reaction yield of 78.3% relative to the racemate.

In addition, when a similar reaction was performed using the same amount of a crude enzyme solution instead of the microbial cell suspension of each transformant, L-Norvaline having an optical purity 100% ee was obtained in a reaction yield of 79.5% relative to the racemate. These results indicate that use of undisrupted microbial cells in the production of L-Norvaline using a transformant having a D-amino acid oxidase activity and a transformant having a leucine dehydrogenase activity and a formate dehydrogenase activity decreases the reactivity.

Reference Example 3

Preparation of Transformant Having Formate Dehydrogenase Activity

PCR was performed using, as a template, a chromosomal DNA obtained from cultivated microbial cells of *Thiobacillus* sp. KNK65MA strain (FERM BP-7671) by the method described in WO03/031626, and DNA primers (Primer-15: Sequence Listing SEQ ID NO: 18 and Primer-16: Sequence Listing SEQ ID NO: 19). PCR was performed in the same manner as in Example 11-1 except that the annealing temperature was set to 50° C. in the PCR conditions. The DNA amplified fragment obtained by the PCR was digested with restriction enzymes NdeI and EcoRI, and the DNA fragment thereof and vector plasmid pUCNT (which can be produced by those of ordinary skill in the art based on the description in the specification of WO94/03613) digested with the same enzymes were ligated using a T4 DNA ligase to give a plasmid designed to be able to express a formate dehydrogenase. By mixing the obtained plasmid with the competent cells of *Escherichia coli* HB101, the competent cells were transformed to prepare a transformant having a formate dehydrogenase activity.

The obtained transformant was inoculated into 6 ml of sterilized medium A in test tube, and aerobically cultured with shaking at 37° C. for 24 hr. Microbial cells were harvested from the obtained culture medium by centrifugation, and a plasmid was extracted using a QIAprep Spin Miniprep Kit (manufactured by QIAGEN) to recover a plasmid designed to be able to express a formate dehydrogenase.

Reference Example 4

Figure 9:
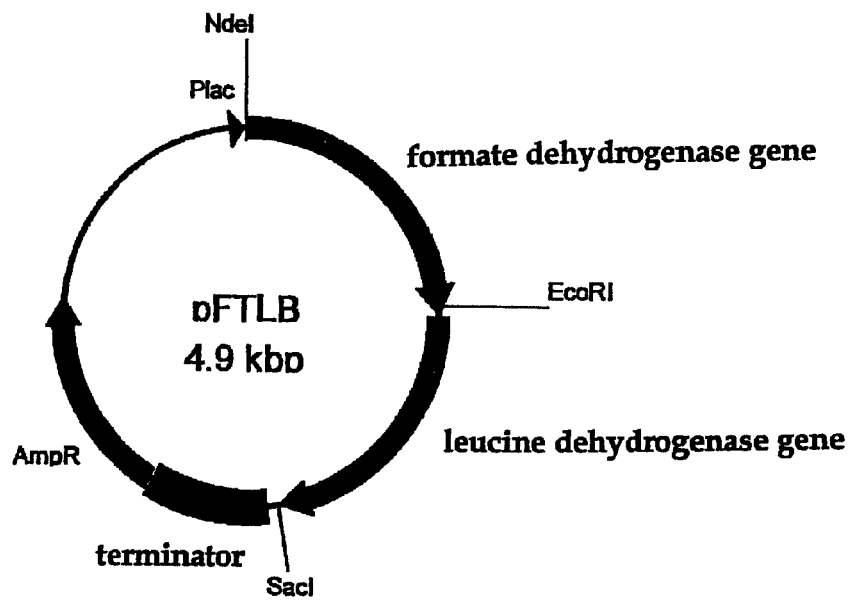
FIG. 9 shows the construction of recombinant plasmid pFTLB containing a leucine dehydrogenase gene and a formate dehydrogenase gene as an embodiment of the present invention.

Preparation of Transformant Having Leucine Dehydrogenase Activity and Formate Dehydrogenase Activity The plasmid designed to be able to express leucine dehydrogenase, which was obtained in Reference Example 2, was digested with EcoRI and SacI, and a DNA fragment containing a leucine dehydrogenase gene was recovered using TaKaRa RECOCHIP (manufactured by Takara Bio Inc.). The recovered DNA fragment and a fragment obtained by digesting the plasmid designed to be able to express formate dehydrogenase, which was obtained in Reference Example 3, with the same enzymes were ligated using a T4 DNA ligase to give plasmid pFTLB shown in FIG. 9, which was designed to be able to express leucine dehydrogenase and formate dehydrogenase in large amounts.

By mixing the obtained plasmid pFTLB with the competent cells of *Escherichia coli* HB101, the competent cells were transformed to prepare a transformant *Escherichia coli* HB101 (pFTLB) having a leucine dehydrogenase activity and a formate dehydrogenase activity.

The obtained transformant *Escherichia coli* HB101 (pFTLB) was inoculated into 6 ml of sterilized medium A in test tube, and aerobically cultured with shaking at 37° C. for 24 hr. Microbial cells were collected from the obtained culture medium by centrifugation, and a plasmid was extracted using QIAprep Spin Miniprep Kit (manufactured by QIAGEN) to recover plasmid pFTLB designed to be able to express leucine dehydrogenase and formate dehydrogenase.

Reference Example 5

Preparation of Transformant Having Phenylalanine Dehydrogenase Activity and Formate Dehydrogenase Activity

Figure 10:
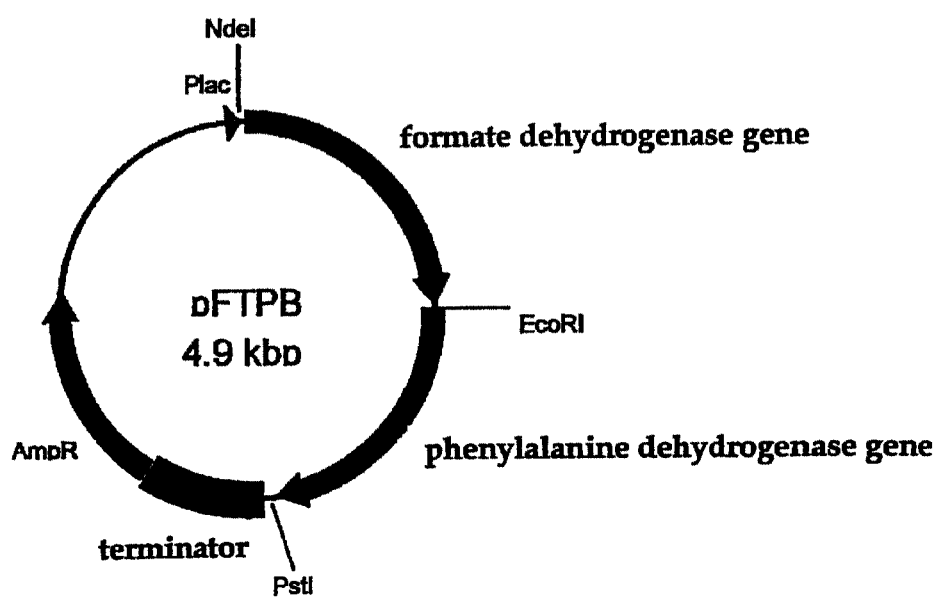
FIG. 10 shows the construction of recombinant plasmid pFTPB containing a phenylalanine dehydrogenase gene and a formate dehydrogenase gene as an embodiment of the present invention.

*Bacillus badius* IAM11059 strain was inoculated into a sterilized medium (1.0% tryptone, 0.5% yeast extract and 0.5% sodium chloride, dissolved in deionized water, pH 7.0 before sterilization), and aerobically cultured with shaking at 30° C. for 48 hr. PCR was performed using, as a template, a chromosomal DNA obtained by the Marmur method from cultivated microbial cells obtained by harvesting microbial cells from the obtained culture medium by centrifugation, and DNA primers (Primer-17: Sequence Listing SEQ ID NO: 20 and Primer-18: Sequence Listing SEQ ID NO: 21). PCR was performed in the same manner as in Example 11-1 except that the annealing temperature was set to 50° C. in the PCR conditions. The DNA amplified fragment obtained by the PCR was digested with restriction enzymes EcoRI and PstI, and the DNA fragment and a fragment obtained by digesting the plasmid designed to be able to express formate dehydrogenase, which was obtained in Reference Example 3, with the same enzymes were ligated using a T4 DNA ligase to give plasmid pFTPB shown in FIG. 10, which was designed to be able to express phenylalanine dehydrogenase and formate dehydrogenase.

By mixing the obtained plasmid pFTPB with the competent cells of *Escherichia coli* HB101, the competent cells were transformed to prepare a transformant *Escherichia coli* HB101 (pFTPB) having a phenylalanine dehydrogenase activity and a formate dehydrogenase activity.

The obtained transformant *Escherichia coli* HB101 (pFTPB) was inoculated into 6 ml of sterilized medium A in test tube, and aerobically cultured with shaking at 37° C. for 24 hr. Microbial cells were collected from the obtained culture medium by centrifugation, and a plasmid was extracted using QIAprep Spin Miniprep Kit (manufactured by QIAGEN) to recover a plasmid designed to be able to express phenylalanine dehydrogenase and formate dehydrogenase.

Reference Example 6

Preparation of Transformant Having D-amino Acid Oxidase Activity

PCR was performed using a vector plasmid pSTV28 (manufactured by Takara Bio Inc.) as a template and DNA primers (Primer-19: Sequence Listing SEQ ID NO: 22 and Primer-20: Sequence Listing SEQ ID NO: 23). The PCR conditions were similar to those in Example 11-1. The DNA amplified fragment obtained by the PCR was digested with restriction enzyme NedI and ligated again using a T4 DNA ligase to give a vector plasmid having a NedI site inserted near the multi-cloning site of the vector plasmid.

The transformant obtained by transforming the competent cells of *Escherichia coli* HB101 by mixing them with the obtained plasmid was inoculated into 6 ml of sterilized medium in test tube (1.6% tryptone, 1.0% yeast extract, 0.5% sodium chloride and 0.01% chloramphenicol, dissolved in deionized water, pH 7.0 before sterilization, chloramphenicol is added after sterilization), and aerobically cultured with shaking at 37° C. for 24 hr. Microbial cells were harvested from the obtained culture medium by centrifugation to recover a plasmid using QIAprep Spin Miniprep Kit (manufactured by QIAGEN).

Figure 11:
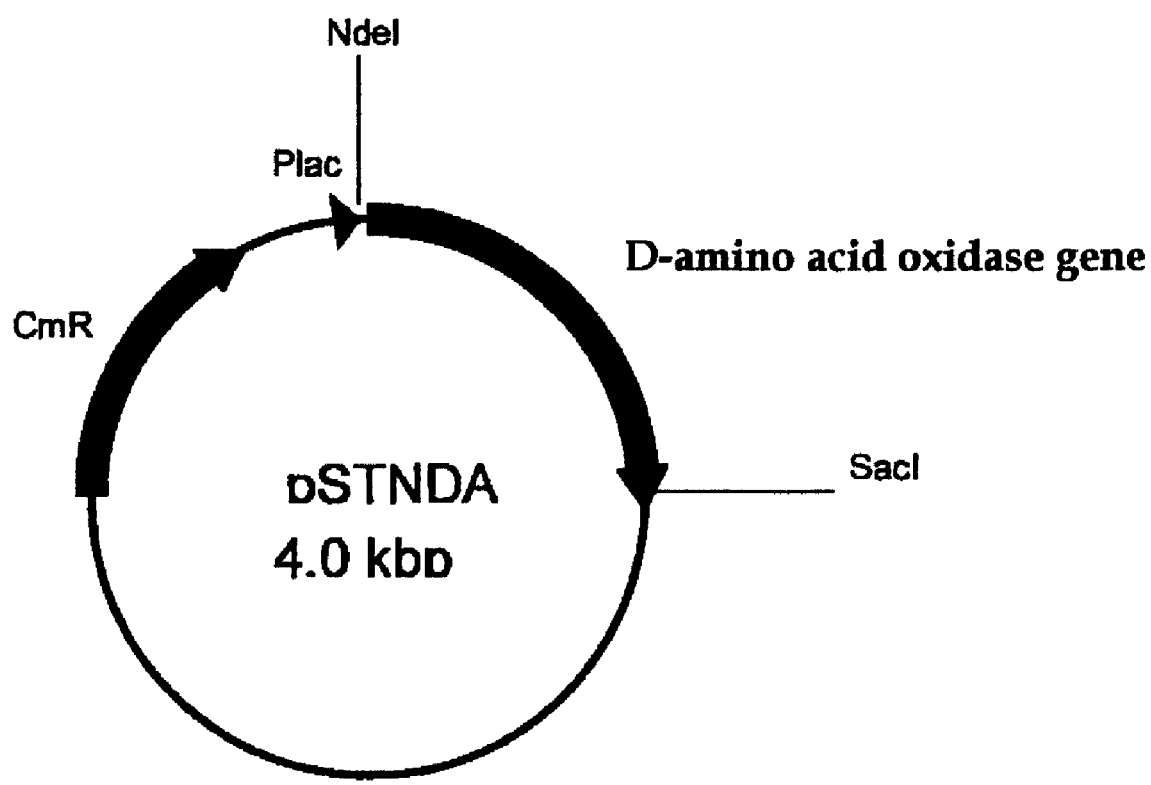
FIG. 11 shows the construction of recombinant plasmid pSTNDA containing a D-amino acid oxidase gene as an embodiment of the present invention.

Next, the expression plasmid pCDA003 designed to be able to express D-amino acid oxidase derived from *Candida intermedia* NBRC0761 strain, which was obtained in Example 6, was digested with restriction enzymes NdeI and SacI, and the DNA fragment containing a D-amino acid oxidase gene was recovered using TaKaRa RECOCHIP (manufactured by Takara Bio Inc.). The recovered DNA fragment and the plasmid obtained by the above-mentioned method, which was digested with the same enzymes, were ligated using a T4 DNA ligase to give plasmid pSTNDA shown in FIG. 11, which was designed to be able to express D-amino acid oxidase.

By mixing the obtained plasmid with the competent cells of *Escherichia coli* HB101, the competent cells were transformed to give a transformant *Escherichia coli* HB101 (pSTNDA) having a D-amino acid oxidase activity. The obtained transformant *Escherichia coli* HB101 (pSTNDA) was inoculated into 6 ml of sterilized medium C in test tube, and aerobically cultured with shaking at 37° C. for 24 hr. Microbial cells were collected from the obtained culture medium by centrifugation to recover plasmid pSTNDA using QIAprep Spin Miniprep Kit (manufactured by QIAGEN).

The invention claimed is:

1. An isolated polynucleotide selected from (a)-(d):
   (a) a polynucleotide comprising a polynucleotide sequence encoding a polypeptide having the amino acid sequence of SEQ ID NO: 1;
   (b) a polynucleotide comprising a polynucleotide sequence encoding a polypeptide having at least 90% amino acid identity to the amino acid sequence of SEQ ID NO: 1.
   (c) a polynucleotide comprising the polynucleotide sequence of SEQ ID NO: 2; and
   (d) a polynucleotide comprising a polynucleotide sequence having at least 90% nucleic acid identity to the polynucleotide sequence of SEQ ID NO: 2,
   wherein said polynucleotide sequence encodes a polypeptide with D-amino acid oxidase activity.

2. A recombinant plasmid comprising the isolated polynucleotide of claim 1.

3. The recombinant plasmid of claim 2, wherein said plasmid further comprises a second polynucleotide sequence encoding a protein with an activity different from that of D-amino acid oxidase.

4. The recombinant plasmid of claim 3, wherein said second polynucleotide sequence encodes a polypeptide having an amino acid dehydrogenase activity or a coenzyme-regenerating activity.

5. An isolated transformant obtained by transforming a host microorganism with the recombinant plasmid of claim 2.

6. The transformant of claim 5, wherein said transformant further comprises a second recombinant plasmid encoding a polypeptide with an activity different from that of D-amino acid oxidase.

7. The transformant of claim 6, wherein said second recombinant plasmid encodes a polypeptide having an amino acid dehydrogenase activity or a coenzyme-regenerating activity.

8. A method of producing D-amino acid oxidase, comprising culturing the isolated transformant of claim 5, accumulating the polypeptide in the culture, and harvesting the polypeptide.

* * * * *